(12) United States Patent
Edel et al.

(10) Patent No.: US 11,579,067 B2
(45) Date of Patent: Feb. 14, 2023

(54) APPARATUS AND METHOD FOR CONCENTRATION OF POLARIZABLE MOLECULES WITHIN A FLUID MEDIUM

(71) Applicant: Imperial Innovations Lilmited, London (GB)

(72) Inventors: Joshua Benno Edel, London (GB); Kevin Joseph Freedman, London (GB)

(73) Assignee: IMPERIAL COLLEGE INNOVATIONS LIMITED, London (GB)

( * ) Notice: Subject to any disclaimer, the term of this patent is extended or adjusted under 35 U.S.C. 154(b) by 124 days.

(21) Appl. No.: 15/735,460

(22) PCT Filed: Jun. 10, 2016

(86) PCT No.: PCT/GB2016/051746
§ 371 (c)(1),
(2) Date: Dec. 11, 2017

(87) PCT Pub. No.: WO2016/198900
PCT Pub. Date: Dec. 15, 2016

(65) Prior Publication Data
US 2018/0164205 A1    Jun. 14, 2018

(30) Foreign Application Priority Data

Jun. 12, 2015  (GB) ..................... 1510322

(51) Int. Cl.
*G01N 27/447*  (2006.01)
*G01N 33/487*  (2006.01)
(Continued)

(52) U.S. Cl.
CPC ..... *G01N 15/1031* (2013.01); *G01N 15/1056* (2013.01); *G01N 27/44791* (2013.01);
(Continued)

(58) Field of Classification Search
CPC .......... G01N 15/1031; G01N 15/1056; G01N 27/44791; G01N 33/48721; G01N 2015/0038
See application file for complete search history.

(56) References Cited

U.S. PATENT DOCUMENTS

| 7,713,395 B1 | 5/2010 | James et al. |
|---|---|---|
| 2004/0127025 A1 | 7/2004 | Crocker, Jr. et al. |

(Continued)

FOREIGN PATENT DOCUMENTS

| WO | 2007058804 | 5/2007 |
|---|---|---|
| WO | 2012073009 | 6/2012 |

(Continued)

OTHER PUBLICATIONS

Combined UK Search and Examination Report for priority application GB 1510322.9, dated Apr. 19, 2016.
(Continued)

*Primary Examiner* — Maris R Kessel
*Assistant Examiner* — Vivian A Tran
(74) *Attorney, Agent, or Firm* — Bradley J. Thorson; DeWitt LLP

(57) ABSTRACT

The disclosure relates to an apparatus and associated method for concentration of polarizable molecules within a fluid medium. The apparatus comprising a structure defining a cavity, having a cross-sectional dimension of 200 nm or less; at least two translocation electrodes positioned relative to the structure to enable generation of a DC electric field passing through the cavity; and at least two trapping electrodes positioned relative to the structure to enable generation of a time-varying electric field proximal to the cavity inlet.

8 Claims, 16 Drawing Sheets

(51) Int. Cl.
G01N 15/10 (2006.01)
G01N 15/00 (2006.01)
(52) U.S. Cl.
CPC ............... *G01N 33/48721* (2013.01); *G01N 2015/0038* (2013.01)

(56) References Cited

U.S. PATENT DOCUMENTS

| | | | |
|---|---|---|---|
| 2004/0181343 | A1 | 9/2004 | Wigstrom et al. |
| 2006/0115971 | A1 | 6/2006 | Bau et al. |
| 2006/0231419 | A1* | 10/2006 | Barth ............... C12Q 1/6825 205/775 |
| 2006/0246497 | A1 | 11/2006 | Huang et al. |
| 2009/0136958 | A1* | 5/2009 | Gershow ............ C12Q 1/6869 435/6.13 |
| 2009/0219647 | A1* | 9/2009 | Hunt ..................... C12N 13/00 360/77.01 |
| 2010/0188109 | A1 | 7/2010 | Edel et al. |
| 2010/0331194 | A1 | 12/2010 | Turner et al. |
| 2011/0027913 | A1* | 2/2011 | Bau ................. G01N 33/54313 436/518 |
| 2011/0168561 | A1 | 7/2011 | Chien et al. |
| 2012/0097539 | A1* | 4/2012 | Qian ..................... B82Y 40/00 204/451 |
| 2012/0282644 | A1 | 11/2012 | Bau et al. |
| 2013/0065795 | A1 | 3/2013 | Allbritton et al. |
| 2013/0068632 | A1 | 3/2013 | Chang et al. |
| 2013/0091607 | A1 | 4/2013 | Gogotsi et al. |
| 2013/0210638 | A1 | 8/2013 | Olson et al. |
| 2013/0240359 | A1 | 9/2013 | Turner et al. |
| 2014/0027287 | A1* | 1/2014 | Peng ..................... B03C 5/026 204/601 |
| 2014/0131202 | A1 | 5/2014 | Peng et al. |
| 2015/0177189 | A1* | 6/2015 | Pourmand ........ G01N 33/48721 204/451 |
| 2015/0219593 | A1* | 8/2015 | Kawai ................ G01N 27/4473 204/549 |
| 2016/0025702 | A1* | 1/2016 | Lindsay ............ G01N 15/1031 204/451 |
| 2016/0146828 | A1* | 5/2016 | Lindsay ............ G01N 33/6818 436/89 |
| 2016/0231307 | A1* | 8/2016 | Xie ..................... G01N 27/4146 |
| 2017/0205330 | A1* | 7/2017 | Huang ............... B01L 3/502761 |
| 2017/0211135 | A1* | 7/2017 | Mir ....................... C12Q 1/6869 |

FOREIGN PATENT DOCUMENTS

| | | | | |
|---|---|---|---|---|
| WO | WO-2012073009 | A2 * | 6/2012 | ......... B81C 1/00087 |
| WO | 2013158021 | | 10/2013 | |
| WO | 2014160036 | | 10/2014 | |
| WO | 2014165168 | | 10/2014 | |
| WO | WO-2015042200 | A1 * | 3/2015 | ............. G16B 30/00 |

OTHER PUBLICATIONS

Squires et al., Nature Biotechnology, "Making It Stick: Convection, Reaction and Diffusion in Surface-Based Biosensors", vol. 26, No. 4, pp. 417-426, Apr. 7, 2008.
Chen et al., Nano Letters, "Probing Single DNA Molecule Transport Using Fabricated Nanopores", vol. 4, No. 11, pp. 2293-2298, Aug. 19, 2004.
Regtmeier et al. Analytical Chemistry, "Dielectrophoertic Manipulation of DNA: Separation and Polarizability", vol. 79, No. 10, pp. 3925-3932, May 15, 2007.
Chou et al., Biophysical Journal, "Electrodeless Dielectrophoresis of Single- and Double-stranded DNA", vol. 83, pp. 2170-2179, Oct. 2002.
Asbury et al., Electrophoresis, "Trapping of DNA by Dielectrophoresis", vol. 23, pp. 2658-2666, 2002.
Gallo-Villanueva et al., Electrophoresis, "DNA Manipulation by Means of Insulator-Based Dielectrophoresis Employing Direct Current Electric Fields", vol. 30, pp. 4195-4205, 2009.
Gascoyne et al, Electrophoresis, "Particle Separation by Dielectrophoresis", vol. 23, pp. 1973-1983, 2002.
Tuukkanen et al., Nanotechnology, "Trapping of 27 BP—8 KBP DNA and Immobilization of Thiol-Modified DNA Using Dielectrophoresis", vol. 18, 295204.
Barik et al., Nano Letters, "Dielectrophoresis-Enhanced Plasmonic Sensing With Gold Nanohole Arrays", vol. 14, pp. 2006-2012, Mar. 19, 2014.
Lesser-Rojas et al., Nano Letters, "Low-Copy Number Protein Detection by Electrode Nanogap-Enabled Dielectrophoretic Trapping for Surface-Enhanced Raman Spectroscopy and Electronic Measurements", vol. 14, pp. 2242-2250, Feb. 28, 2014.
Yeo et al, Nanotechnology, "Dielectrophoretic Concentration of Low-Abundance Nanoparticles Using a Nanostructured Tip", vol. 23, pp. 485707, 2012.
Siwy et al, Journal of the American Chemical Society, "Protein Biosensors Based on Biofunctionalized Conical Gold Nanotubes", vol. 127, pp. 5000-5001, 2005.
Siwy et al, Journal of the American Chemical Society, "Conical-Nanotube Ion-Current Rectifiers: The Role of Surface Charge", vol. 126, pp. 10850-10851, 2004.
Ivanov et al, ACS Nano, "On-Demand Delivery of Single DNA Molecules Using Nanopipets", vol. 9, No. 4, pp. 3587-3595, 2015.
Lan et al, Journal of the American Chemical Society, "Pressure-Dependent Ion Current Rectification in Conical-Shaped Glass Nanopores", vol. 133, pp. 13300-13303, 2011.
Siwy et al, Physical Review Letters, "Fabrication of a Synthetic Nanopore Ion Pump", vol. 89, pp. 198103, 2002.
Wei et al, Analytical Chemistry, "Current Rectification at Quartz Nanopipet Electrodes", vol. 69, pp. 4627-4633, 1997.
Tabard-Cossa et al, Nanotechnology, "Noise Analysis and Reduction in Solid-State Nanpores", vol. 18, pp. 305505, 2007.
Steinbock et al, ACS NONO, "DNA Translocation Through Low-Noise Glass Nanopores", vol. 7, No. 12, pp. 11255-11262, 2013.
Eggeling et al, Analytical Chemistry, "Photobleaching of Fluorescent Dyes Under Conditions Used for Single-Molecule Detection: Evidence of Two-Step Photolysis", vol. 70, pp. 2651-2659, Jul. 1, 1998.
Giloh et al, Science, "Fluorescence Microscopy: Reduced Photobleaching of Rhodamine and Fluorescein Protein Conjugates by N-Propyl Gallate", vol. 217, pp. 1252-1255, Sep. 1982.
Regtmeier et al, Analytical Chemistry, "Dielectrophoretic Trapping and Polarizability of DNA: The Role of Spatial Conformation", vol. 82, No. 17, pp. 7141-7149, Sep. 1, 2010.
Marc Gershow and J.A. Golovchenko, Nature Nanotechnology, "Recapturing and Trapping Single Molecules With a Solid-State Nanopore", vol. 2, pp. 775-779, Dec. 2, 2007.
Panja et al, Journal of Physics: Condensed Matter, "Through the Eye of the Needle: Recent Advances in Understanding Biopolymer Translocation", vol. 25, pp. 413101, Sep. 1, 2013.
Wanunu et al, Nature Nanotechnology, "Electrostatic Focusing of Unlabelled DNA Into Nanoscale Pores Using a Salt Gradient", vol. 5, pp. 160-165, Feb. 2010.
P.J. Burke, Encyclopedia of Nanoscience and Nano Technology, "Nanodielectrophoresis: Electronic Nanotweezer", vol. 6, pp. 623-641, (2004).
International Preliminary Report on Patentability for PCT Application PCT/GB2016/051746.

\* cited by examiner

APPARATUS AND METHOD FOR CONCENTRATION OF POLARIZABLE MOLECULES WITHIN A FLUID MEDIUM

CROSS-REFERENCED TO RELATED APPLICATIONS

This application claims priority from Application PCT/GB2016/051746, filed Jun. 10, 2016, which is deemed incorporated by reference in its entirety in this application.

STATEMENT REGARDING FEDERALLY SPONSORED RESEARCH OR DEVELOPMENT

Not applicable.

BACKGROUND OF THE INVENTION

I. Field of the Invention

The present disclosure relates to an apparatus and method for concentration of polarizable molecules within a fluid medium and, in particular although not exclusively, to RNA/DNA sequencing.

II. Discussion of the Prior Art

Nanopores are a rapidly growing technology for DNA sequencing. The ability to efficiently detect single molecules in solution has been has only recently come to fruition where technologies, such as those aimed towards DNA sequencing, offer unprecedented advantages in terms of sensitivity and diagnostic utility. One exceptionally promising route has been the use of single molecule detection strategies based around nanopores. However, a complexity of such analysis is that the dominant mechanism of capture and detection of individual molecules is diffusion-limited making the efficiency low. Consequently, sub-pM samples become difficult to statistically represent, especially considering that the capture volume of a nanopore (3 µm capture radius≈56 µm$^3$) is typically 10$^8$ times smaller than the total sample volume. In fact, this problem extends further than nanopore-based sensors and is a fundamental problem with surface-based biosensors.

SUMMARY OF THE INVENTION

According to a first aspect of the present invention there is provided an apparatus for concentration of polarizable molecules within a fluid medium, the apparatus comprising:
- a structure defining a cavity, having a cross-sectional dimension of 200 nm or less;
- at least two translocation electrodes positioned relative to the structure to enable generation of a direct current (DC) electric field passing through the cavity; and
- at least two trapping electrodes positioned relative to the structure to enable generation of a time-varying electric field proximal to the cavity inlet.

The apparatus may enable efficient single molecule nanopore sensing at femtomolar concentrations using dielectrophoretic trapping by combining sensing using a nanoscale cavity, or nanopore, and dielectrophoresis (DEP). DEP may be used as the mechanism to trap molecules near an opening of the nanopore. The combination of nanoscale sensing and DEP enables an increase in the number of molecules being sensed in the bulk solution as well as a reduction in the limit of detection.

The time-varying electric field may interact with the molecule in order to trap the molecule in a region adjacent to the opening of the cavity using dielectrophoresis (DEP). The cavity may be defined by the structure comprises a nanopore. The structure defining the cavity may comprises any of: a solid-state structure; a dielectric material structure; a biological structure; a hybrid biological structure-polymer structure. One of the translocation electrodes and one of the trapping electrodes may be the same electrode. The translocation electrodes may include a common electrode with the trapping electrodes. The translocation electrodes may include a different electrode to the trapping electrodes. The structure defining the cavity may comprise a pipette. The pipette may be a first pipette. The apparatus may further comprise a second pipette. The, or each, pipette may have an aperture having a cross-sectional dimension of 200 nm or less.

The at least two trapping electrodes may comprise a first trapping electrode. The at least two trapping electrodes may comprise a second trapping electrode. The at least two translocation electrodes may comprise a first translocation electrode. The at least two translocation electrodes may comprise a second translocation electrode.

The first trapping electrode may be provided by a carbon deposit in the first pipette. The second trapping electrode may be provided by a carbon deposit in the second pipette. The first translocation electrode may be disposed within the first pipette. The second translocation electrode may be disposed within the second pipette. The first pipette may comprise a first cavity. The first pipette may comprise a second cavity. The second pipette may comprise a first cavity. The second pipette may comprise a second cavity. Within a pipette, the first cavity may be separated from the second cavity by a barrier such that fluid flow within the pipette from the first cavity to the second cavity is prevented.

The trapping electrodes may extend over an external surface of the structure. Another of the trapping electrodes may extend over a surface of a substrate confining the fluid medium-upstream of an inlet of the cavity. Another of the trapping electrodes may be positioned in a fluid medium upstream of an inlet of the cavity.

The apparatus may further comprise a controller. The controller may be configured to apply an alternating current (AC) voltage to the at least two trapping electrodes. The controller may be configured to apply a DC voltage to the at least two translocation electrodes. The apparatus may further comprise an AC voltage source and/or a DC voltage source.

The controller may be configured to cease applying the AC voltage before commencing application of the DC voltage. The controller may be configured to apply the AC voltage and the DC voltage simultaneously in order to retard translocation.

According to a further aspect of the present invention there is provided a protein detector comprising the apparatus. According to a further aspect of the present invention there is provided a DNA, RNA or protein sequencer comprising the apparatus. A DNA, RNA or protein mapper is also disclosed.

According to a further aspect of the present invention there is provided a method of concentrating polarizable molecules within a fluid medium, comprising:
- trapping molecules proximal to an inlet of a structure defining a cavity by generating a time varying electric field proximal to the inlet using at least two trapping electrodes positioned relative to the structure;

performing translocation by generating an electric field passing through the cavity by applying a direct current to at least two translocation electrodes positioned relative to the structure, in which the cavity has a cross-sectional dimension of 200 nm or less.

According to a further aspect of the present invention there is provided a method of DNA, RNA or protein sequencing comprising providing a fluid containing a DNA, RNA or protein molecule to be sequenced to the sequencer. Also disclosed is a method of concentrating a polarizable molecule using the apparatus.

According to a further aspect of the present invention there is provided a method of forming a structure for concentrating polarizable molecules within a fluid medium, the method comprising:

forming a first pipette with an aperture having a cross-sectional dimension of 200 nm or less;

depositing carbon to provide a first trapping electrode in the first pipette;

providing a first translocation electrode associated with the first pipette; and inserting at least a portion of the first pipette into a fluid tube defining a reservoir for the fluid medium.

The method may comprise forming a second pipette, in which each pipette has an aperture having a cross-sectional dimension of 200 nm or less. The method may comprise depositing carbon to provide a second trapping electrode in the second pipette. The method may comprise providing a second translation electrode associated with the second pipette. The method may comprise inserting at least a portion of the first and second pipettes into a fluid tube to define a reservoir for the fluid medium between the first and second pipettes. The carbon may be deposited by combusting a substance within the tube. Each pipette may define a first cavity and a second cavity. The trapping electrodes may be deposited in the respective first cavities. The translocation electrodes may be provided in the respective second cavities.

DESCRIPTION OF THE DRAWINGS

Embodiments of the present invention are now described, by way of example only, with reference to the accompanying drawings, in which.

DETAILED DESCRIPTION

Figure 1A:
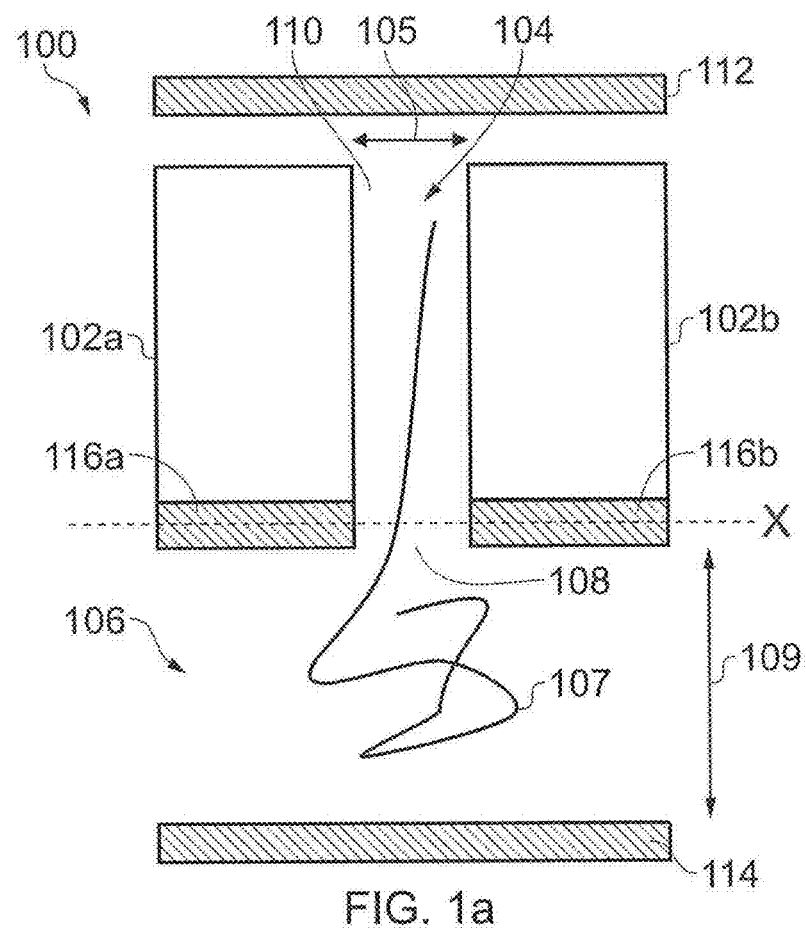
FIGS. 1a to 1d illustrate schematic views of a number of apparatus for concentration of polarizable molecules within a fluid medium.

The present disclosure relates to combining sensing using a nanoscale cavity, or nanopore, and dielectrophoresis (DEP). DEP may be used to trap molecules near an opening of the nanopore. The combination of nanoscale sensing and DEP enables an increase in the number of molecules being sensed in the bulk solution as well as a reduction in the limit of detection. The use of dielectrophoretic trapping in combination with electrophoresis within a nanopore may at least partially address problems associated with sensing a disproportionate low ratio of molecules in a bulk solution to those actually being delivered to and sensed by the nanopores. Using metalized nanopipettes or other nanopore structures, DNA may be captured from a much larger volume and concentrated at the nanopipette tip using an AC voltage. The impact of this technology may be enormous as biomarkers may be detected at concentrations as low as 5 fM which is approximately 1000× more efficient than some existing methods.

FIGS. 1a to 1d illustrate a number of apparatus for concentration of polarizable molecules within a fluid medium. The apparatus may also be used to detect, sequence or map proteins, RNA or DNA.

FIG. 1 a shows an apparatus 100 comprising a structure 102a, 102b defining a cavity 104. A reservoir 106 of fluid is provided adjacent to the cavity. The reservoir may have a depth 109 of a few microns, such as 50 or 100 microns, for example. The fluid may be a solution, including an aqueous solution, colloid or suspension. The fluid comprises one or more molecules 107, such as a protein, a virus, RNA or DNA. The molecules 107 may be intrinsically polarizable, or polar molecules. Alternatively, molecules 107 may comprise a non-polarizable or weakly-polarizable molecule (which may be the target, or molecule of interest) bound to a polarizable molecule in order to enable interaction with the apparatus 100. A micro- or nano-particle may be provided to pull a non-polarizable or weakly polarizable molecule into the cavity 104.

The cavity 104 defines a flow path for fluid between an inlet of the cavity 104, which may be referred to as an upstream aperture 108, and an outlet of the cavity 104, which may be referred to below as a downstream aperture 110. The reservoir 106 is provided adjacent to, and in fluid communication with, the upstream aperture 108 of the cavity 104. In the example shown, the upstream aperture 108 is of the same cross-sectional dimension 105 as the downstream aperture 110, although this need not necessarily be the case in other examples.

The size of the aperture is such that molecules 107 from the fluid can pass into the cavity 104. The upstream aperture 108 has a cross-sectional dimension 105 of 200 nm. In some examples, the upstream aperture 108 may have a cross-sectional dimension of less than 30 nm, or even less than 3 nm. The cavity 104 may be considered to be a nanopore due to its nano-scale dimensions.

Two translocation electrodes 112, 114 are positioned relative to the structure 102a, 102b to enable generation of a direct current (DC) electric field passing through the cavity. The translocation electrodes 112, 114 may comprise a metal or metallic conductor. The apparatus may further comprise a DC voltage source (not shown) coupled to the respective translocation electrodes 112, 114. The translocation electrodes 112, 114 may be considered to generate a translocation field when in use. That is, an electric field that is configured to draw molecules 107 from the fluid in the reservoir through the upstream aperture 108 of the cavity 104, through the cavity and, optionally, through the downstream end 110 of the cavity 104. In order to provide this functionality, a first translocation electrode 112 is provided adjacent to the downstream aperture 110 of the cavity 104 and a second translocation electrode 114 is provided on an opposing side of the reservoir 106 such that the structure 102a, 102b (as well as the reservoir 106) is between the two translocation electrodes 112, 114.

The translocation electrodes 112, 114 may also be used to measure an ionic current of fluid within the cavity 104, as well as to provide an electromotive force to the fluid. The partial occlusion of the cavity by the presence of a molecule within the fluid may be signaled by a reduction in the current measured between the translocation electrodes 112, 114. Different molecules tend to induce a different level of occlusion and so result in a different characteristic current. The translocation current may therefore be used in order to characterize the molecule passing through the cavity 104 and so may be used to perform analyte (e.g. protein, DNA/RNA) detection, sequencing or mapping using techniques that are known in the art. The apparatus may also comprise a current monitor coupled to the translocation electrodes 112, 114 in order to measure the translocation current or another current through the cavity.

The apparatus also comprises two trapping electrodes 114, 116a, 116b. The trapping electrodes 114, 116a, 116b are positioned relative to the structure to enable generation of an inhomogeneous or non-uniform electric field proximal to the cavity inlet on the application of a time-varying voltage. A time-varying voltage is a voltage that varies substantially as a function of time. An alternating current (AC) voltage or alternating voltage are examples of time-varying voltages, as is an AC voltage with a DC voltage offset. A time-varying voltage does not necessarily need to change sign. That is, it need not necessarily change from being a positive voltage to a negative voltage and vice versa. The time-varying voltage may have a sinusoid wave function or other wave function such as a triangular or square wave function. The time-varying voltage may also be symmetrical or asymmetrical. The time-varying voltage may also be periodic or aperiodic, regular or irregular.

The trapping electrodes comprise a first trapping electrode 116a, 116b and a second trapping electrode 114. The first trapping electrode 116a, 116b extends over an external surface of the structure 102a, 102b at the same end of the structure as the upstream aperture 108 and adjacent to the reservoir 106. In this example, the second translocation electrode 114 and the second trapping electrode 114 are provided by the same electrode. The trapping electrodes 114, 116a, 116b in this example are provided on opposing sides of fluid within the reservoir 106. In an alternative arrangement, one or more of the trapping electrodes 114, 116a, 116b may be positioned in the fluid upstream of the upstream aperture 108 of the cavity 104.

DEP-based methods can apply forces to biomolecules of interest (i.e. DNA, RNA proteins) to concentrate them using an inhomogeneous electric field. In the case of DNA, a non-uniform electric field acts on induced dipole moments to attract the molecule towards the point of maximum electric field gradient $(\nabla|E|^2)^3$.

Dielectrophoresis (DEP) can be employed within fluidic system to enhance the transport of molecules, increase the concentration of molecular species, perform separation processes, as well as stretch and immobilize molecules. The apparatus described herein may utilize the polarizability of an analyte to apply forces to the molecule and manipulate its position. Manipulating the location of nanoscale objects using an electric field holds practical applications in analytical devices since discerning molecular identity typically relies on (1) mixing with a recognition agent and (2) obtaining a large enough concentration for detection. Despite the obvious usefulness of DEP, the technique has seen limited use within nanopore systems due to the complexities surrounding integrating both AC and DC electrodes into the recording setup without introducing excess noise.

In general, the trapping electrodes 114, 116a, 116b are arranged in order to provide a region of inhomogeneity in a proximal region adjacent to the upstream aperture 108 in order to trap and therefore concentrate molecules 107 from the fluid within the reservoir 106 in the proximal region and so increase the number of molecules 107 that are likely to be drawn into the cavity 104 by the translocation electric field provided by the translocation electrodes 112, 114.

The apparatus may also comprise a controller (not shown) configured to operate the translocation electrodes 112, 114 and the trapping electrodes 114, 116a, 116b. The controller may be implemented by hardware or software, or a combination of hardware and software. The controller may be configured to perform a method comprising applying an AC voltage to the two trapping electrodes 114, 116a, 116b and applying a DC voltage to the two translocation electrodes 112, 114.

In a first mode, the controller is configured to apply the AC voltage to the two trapping electrodes 114, 116a, 116b before commencing application of the DC voltage to the at least two translocation electrodes 112, 114. By applying the AC voltage at a separate time to the DC voltage, interference or crosstalk from the AC voltage to the DC voltage can be reduced and so the accuracy and/or precision with which an ionic current within the cavity 104 can be measured may be improved.

In a second mode, the controller is configured to apply the AC voltage and the DC of voltage simultaneously in order to retard translocation. The translocation is slowed down because of the simultaneous application of two opposing forces: the DEP trapping force and the translocation electrophoresis force. Retarding the translocation is useful in some applications because otherwise the rate of electrically-driven translocation may be too rapid for information regarding the molecules 107 that are under analysis to be performed efficiently and accurately.

Figure 1B:
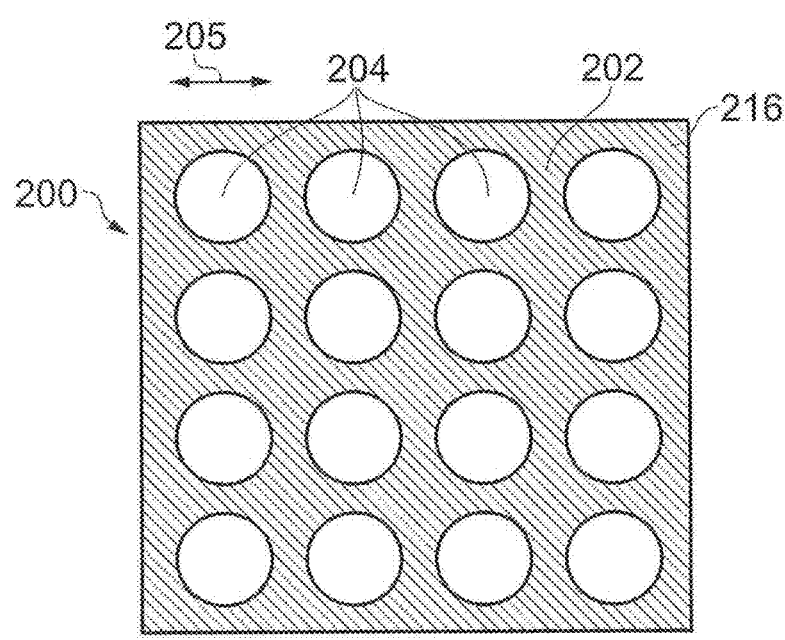

FIG. 1b illustrates a schematic of an apparatus 200 comprising plurality of cavities 204 defined within a structure 202. The plane of the structure 202 shown in FIG. 1b can be taken through the cross-section marked X in FIG. 1a. The provision of a plurality of cavities enables a respective plurality of molecules to be analysed in parallel and so the speed of analysis using the apparatus 200 may be increased compared to an apparatus comprising only a single cavity in which molecules may only be analysed in series.

The first trapping electrode 216 is provided as a continuous layer on the surface of the structure 202 adjacent to, and surrounding, the upstream apertures of the cavities 204. Alternatively, the first trapping electrode may be provided by discontinuous islands of conductive material on the surface of the structure 202 between the cavities 204. In that case, the individual apertures/cavities 204 may have mutually independent AC trapping.

Each of the cavities 204 has substantially the same cross-sectional dimension 205 as one another. The cross-sectional dimension is a diameter because the cavities 204 are generally circular.

The structure defining the cavity may comprises any of: a solid-state structure; a dielectric material structure; a biological structure; a hybrid biological structure-polymer structure.

Figure 1C:
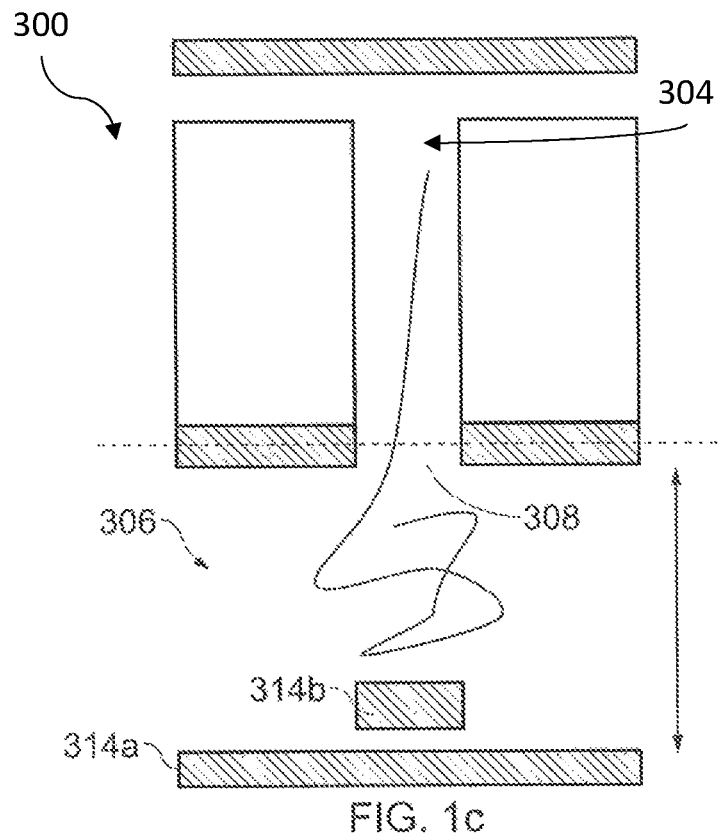

FIG. 1c illustrates another apparatus 300 and is generally similar to the apparatus described with respect to FIG. 1a. In this example, the second translocation electrode 314a and the second trapping electrode 314b are provided by different electrodes. The trapping electrodes in this example are provided on opposing sides of a portion of the fluid within the reservoir 306. The second trapping electrode is positioned in the fluid upstream of the upstream aperture 308 of the cavity 304.

Figure 1D:
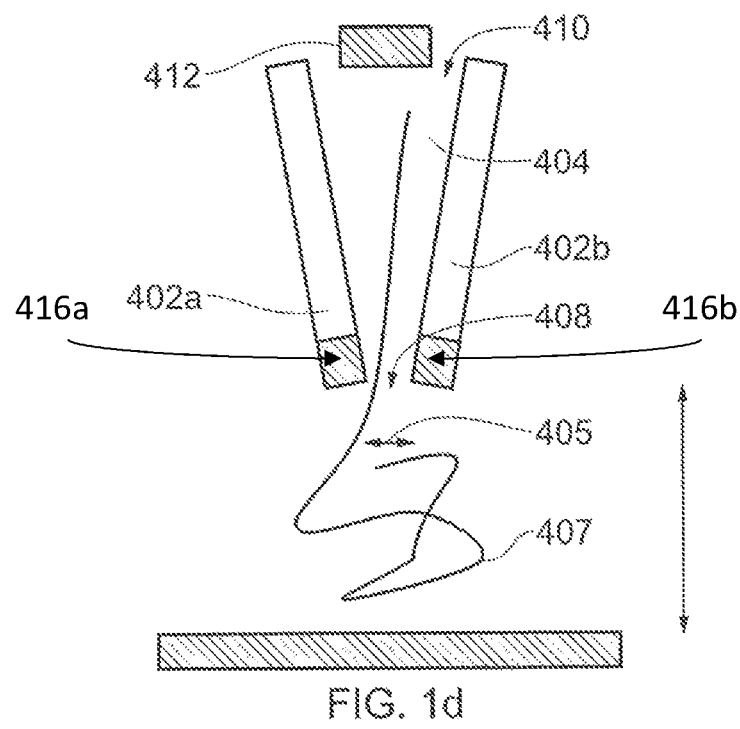

FIG. 1d illustrates a cross-sectional schematic of another apparatus for concentration of polarizable molecules 407 within a fluid medium. The structure 402a, 402b defining the cavity comprises a pipette in this example. The structure 402a, 402b has a tubular tapered wall defining the cavity 404. The upstream aperture 408 may have a similar cross-sectional dimension 405 to that described with reference to FIG. 1. The downstream aperture 410 has a greater cross-sectional dimension than that of the upstream aperture 408 due to the taper.

The first translocation electrode 412 is provided adjacent to the downstream aperture 410. Alternatively, the first translocation electrode 412 may be provided on a surface of the structure 402a, 402b, for example. In either case, first translocation electrode 412 may be provided either inside or outside of the structure 402a, 402b, and may be connected to an inside of the structure 402a, 402b. Also in either case, the first translocation electrode 412 may be separate from the first trapping electrode 416a, 416b. The electrodes 412, 416a, 416b may be separate in that there is no direct electrical connection between them.

The first trapping electrode 416a, 416b is provided on the wall of the structure 402a, 402b. In this example, the first trapping electrode 416a, 416b is provided adjacent to the upstream aperture 408. The first translocation electrode 416a, 416b may extend along an outer surface of the structure away from the upstream aperture 408.

Devices or electrode configurations that make use of DEP trapping may come in a variety of forms and configurations which dictate the shape of the trapping volume (i.e. the volume where the DEP force overcomes Brownian motion) and the strength of the electric field gradients. Typically the distance between the two electrodes responsible for the DEP may be on the micrometer length scale to make trapping feasible. Although two-dimensional (2D, i.e. planar) electrodes are easy to fabricate, several studies have shown that three-dimensional (3D) trapping using metallic tips is more efficient and leads to stronger DEP forces. Metallic tips also offer several key advantages over 2D electrodes such as having a (i) 3D trapping volume, (ii) being able to control the electrode gap distance and therefore the field gradient forces, and (iii) added enhancement due to the sharpness of the metallic tip.

Building on the advantages of the 3D metallic tip electrodes used in DEP trapping experiments, glass nanopipettes can be functionalized with a noble metal (gold) to allow for DEP trapping of DNA as well as ionic current sensing of the DNA as it translocates the nanopore. High gradient forces efficiently trap DNA and therefore it is often useful to determine the spatial distribution of the nonuniform electromagnetic fields around the tip of the nanopipette. The time-averaged dielectrophoretic force acting on a spherical particle of radius R is given by $$F_{DEP}(\omega) = \pi \varepsilon_m R^3 Re(f_{CM}(\omega)) \nabla |E|^2$$

Here $\varepsilon$ denotes the real permittivity of the medium, E is the total electric field, and $f_{CM}(\omega)$ is the frequency-dependent Clausius-Mossotti factor given by:

$$f_{CM}(\omega) = \frac{\varepsilon_p^*(\omega) - \varepsilon_m^*(\omega)}{\varepsilon_p^*(\omega) + 2\varepsilon_m^*(\omega)}$$

where $\varepsilon_p^*$ and $\varepsilon_m^*$ are the particle and medium complex permittivities. The radius of the particle and the Clausius-Mossotti factor are determined by the experimental setup (e.g. molecule being trapped, and the medium it is suspended), however the gradient electric field is a controllable parameter which can be optimized to enhance the trapping capability of the nanopipette. In the following simulations, it is the $\log(\nabla |E|^2)$ which is reported.

The construction, testing and characterisation of an apparatus in accordance with the principles discussed above are described in the following sections and with reference to FIGS. 2 to 6.

Nanopipette Fabrication and Characterization.

Figure 2:
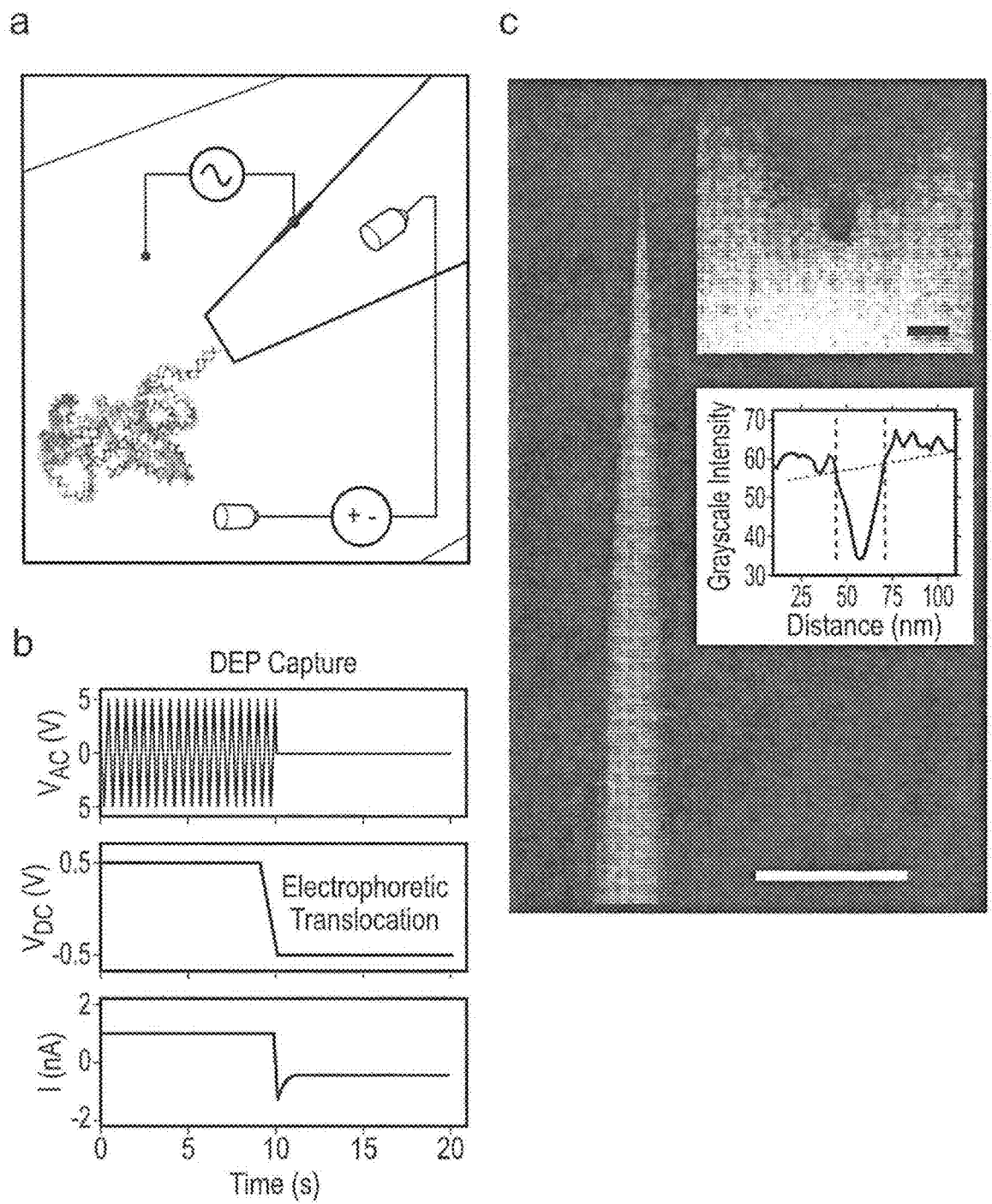
FIGS. 2 to 5 illustrate various views and profiles associated with experimental validation of an apparatus similar to that described with reference to FIG. 1d.
Figure 2:
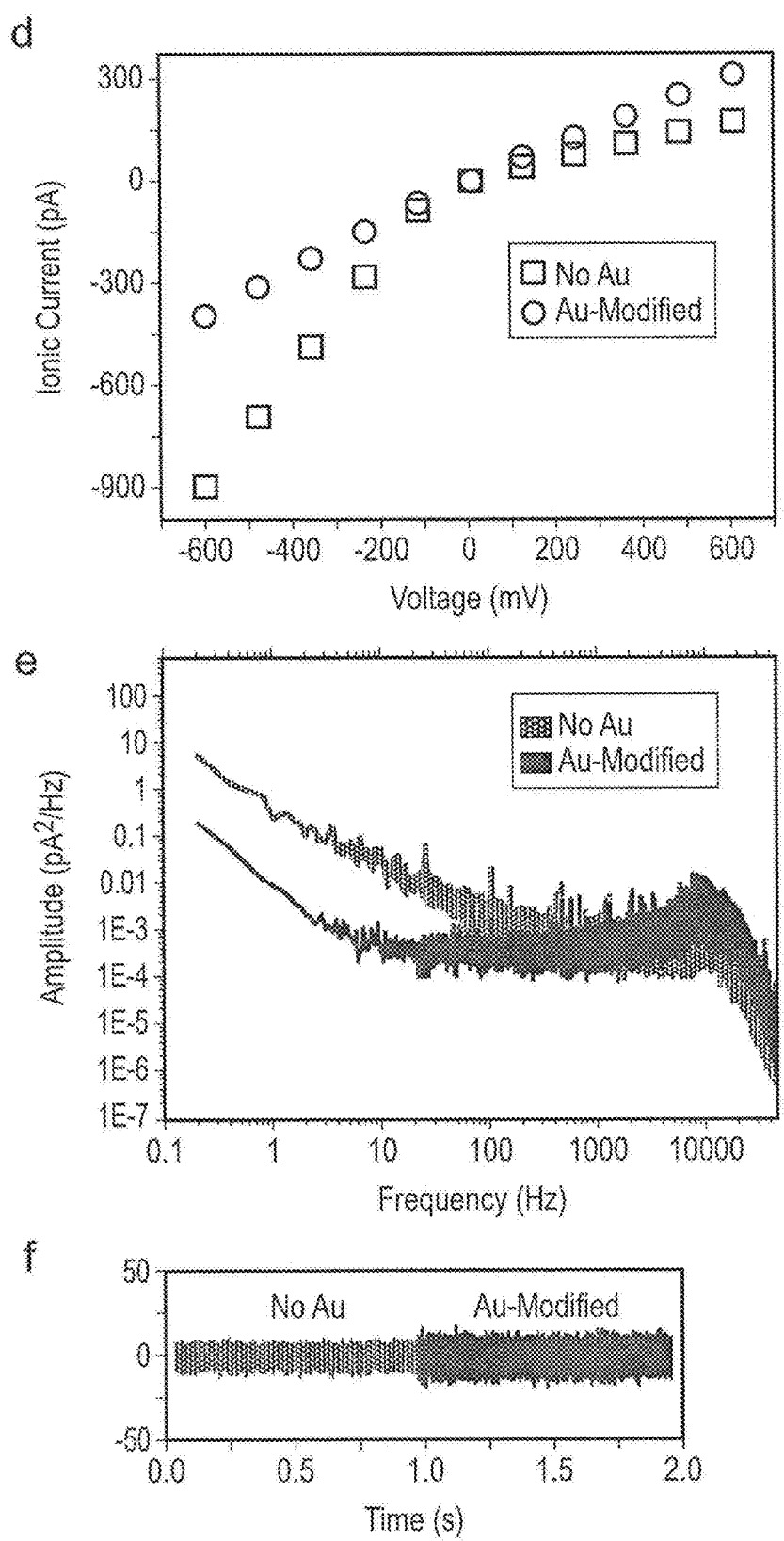

FIG. 2 shows an experimental setup and characterization of a gold-coated nanopipette. In particular, FIG. 2 illustrates:
  (a) Schematic of DNA being threaded through the tip of a gold-coated nanopipette.
  (b) Voltage-protocol used for DNA pre-concentration (DEP capture via AC voltage) and subsequent translocation (electrophoretic capture via DC voltage).
  (c) SEM of a gold-coated nanopipette; scale bar=5 μm (insets: SEM and intensity line plot of the tip visualized parallel to the barrel; Scale bar=50 nm).
  (d) Current-voltage curves for glass nanopipettes before and after gold coating. Gold coating thickness was approximately 5 nm.
  (e) Power spectral density of pipettes under a negative 500 mV voltage bias.
  (f) Baseline subtracted time traces of the pipettes prior to and after gold coating at a negative 500 mV voltage bias.

Using metalized nanopipettes, DNA may be captured from a much larger volume and concentrated at the nanopipette tip by applying an AC voltage to the metallized layer surrounding the nanopipette. The AC and DC voltages are applied to the system using two Au-electrodes and two Ag/AgCl electrodes, respectively (FIG. 2a-b). The benefits of DEP on genetic analyses may be enormous due to the need for ultra-sensitive methods which can analyze low-concentrations of genomic DNA.

Nanopipettes may be manufactured by heating and pulling glass capilliaries until nanometer-sized openings are formed at the tip. Nanopipettes were fabricated using a P-2000 laser puller (Sutter Instrument Co.) from quartz capillaries with an outer diameter of 1.0 mm and an inner diameter of 0.5 mm (QF100-50-7.5; Sutter Instrument Co). Nanopipettes were fabricated using a two-line protocol: 1) HEAT: 575; FIL: 3; VEL: 35; DEL: 145; PUL: 75, followed by 2) HEAT: 900; FIL: 2; VEL: 15; DEL: 128; PUL: 200. Pipettes were then coated with 5 nm of gold (Quorum Technologies; Q150R S) and used within several weeks of coating. In rare cases (approximately one in twenty pipettes) gold would delaminate from the pipette and this was observed optically by the DNA being attracted upstream from the tip to where the gold layer was still intact. It was more likely to see the delamination of gold from the second gold electrode: a glass slide coated with 5-10 nm of gold. The conical geometry of the pipette may have attributed to the stability of the gold which we also observed to increase over time. In cases where pipettes had to be used immediately after gold coating, a thin layer of chromium could be used to increase the level of gold adhesion.

When biological molecules are passed through the opening, the exclusion of ions causes a decrease in bulk ion flow thereby allowing single molecules to be detected. Quartz glass capillaries with an outer diameter of 1 mm and an inner diameter of 0.5 mm were plasma cleaned and used throughout all the experiments. The capillary ends were pulled apart while the middle of the capillary was heated by a $CO_2$ laser (P2000, Sutter Instruments). At the end of the pulling procedure, two identical nanopipettes are formed with the same pore dimensions (pulling parameters provided in Methods section). Immediately following the pulling procedure, the nanopipettes were coated with 5 nm of gold. After fabrication, nanopipette diameters as well as gold layer conformity were measured by scanning electron microscopy (SEM). Although thicker gold layers were initially tested and proved successful for DEP trapping, thinner gold layers were preferred since longer deposition times had a higher probability of blocking the pore. As for the lower limit of gold deposition, sub-5-nm gold layers had a lower success rate which was due to the lack of conformal coating and/or higher electrical resistance.

The SEM images of the nanopipettes show that after gold coating, the pore is unblocked and has an inner diameter of 25±4 nm (FIG. 2c). The nanopipettes were further characterized by filling the barrel of the pipette with 1 mM KCl and lowering the tip into a bath also filled with 1 mM KCl. When a voltage bias is applied between the Ag/AgCl electrodes, ions traverse the pore and contribute to a stable ionic current. Using bare quartz nanopipettes, the current-voltage (I-V) curve showed rectification (i.e. unequal conduction depending on voltage polarity) consistent with that expected by negatively-charged conical glass nanopores. Upon coating with gold, the rectification behavior is reduced but is still present ($|I_{-600\ mV}/I_{600\ mV}|=1.27$) compared to the bare pipette ($|I_{-600\ mV}/I_{600\ mV}|=4.8$) (FIG. 2d). The decrease in rectification suggests the presence of gold affected the surface charge of the nanopipette however the effects are inconsequential since both pipettes allow the passage of DNA through the tip. The noise level of the devices after gold deposition showed a >1 order of magnitude reduction in low frequency 1/f noise typically associated with conductance fluctuations (flicker noise) and a mild increase in higher frequency noise typically attributed to capacitance (FIG. 2e). The peak-to-peak voltage comparison (FIG. 2f) shows a minimal increase with the gold coated nanopipettes but the increase is insignificant when compared to the conductance change expected from DNA translocations (200-500 pS).

Fluorescence Measurements

Double stranded DNA with a length of 10 kbp and with a stock concentration of 500 µg/ml were obtained from New England Biolabs. DNA solutions (500 pM, 50 pM, 5 pM, 500 fM, 50 fM, and 5 fM) were prepared by serial dilution. For fluorescence measurements, DNA was incubated with YOYO-1 (Molecular Probes) at a ratio of 5 base pairs per molecule. Images and video were collected by a 60× water-immersion objective and directed to an electron multiplying CCD (emCCD) camera (Cascade II, Photometrics). The CCD camera has a pixel size of 16 µm, however, when used in conjunction with the 60× objective, the final effective pixel size was 266 nm.

Figure 3:
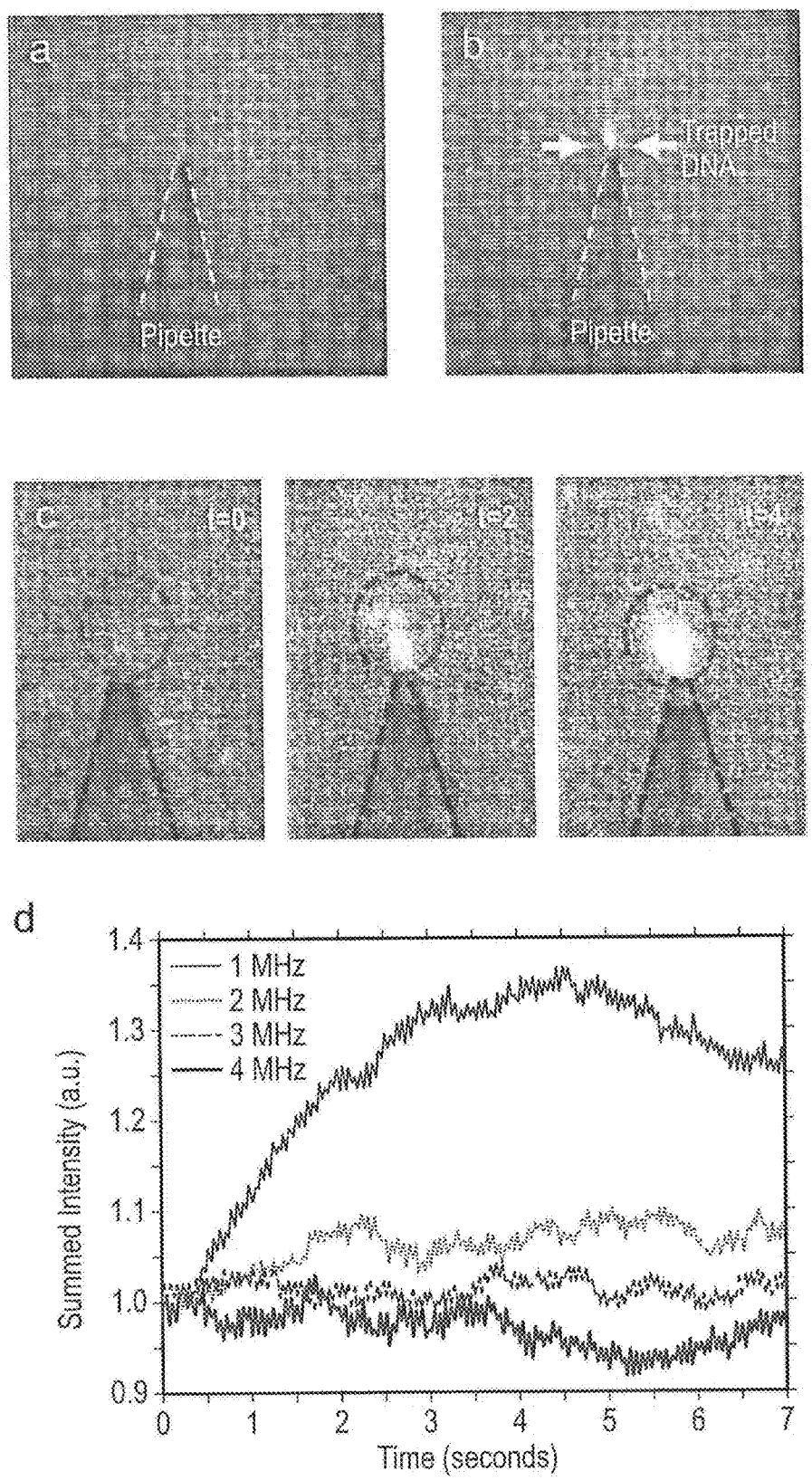
Figure 3:
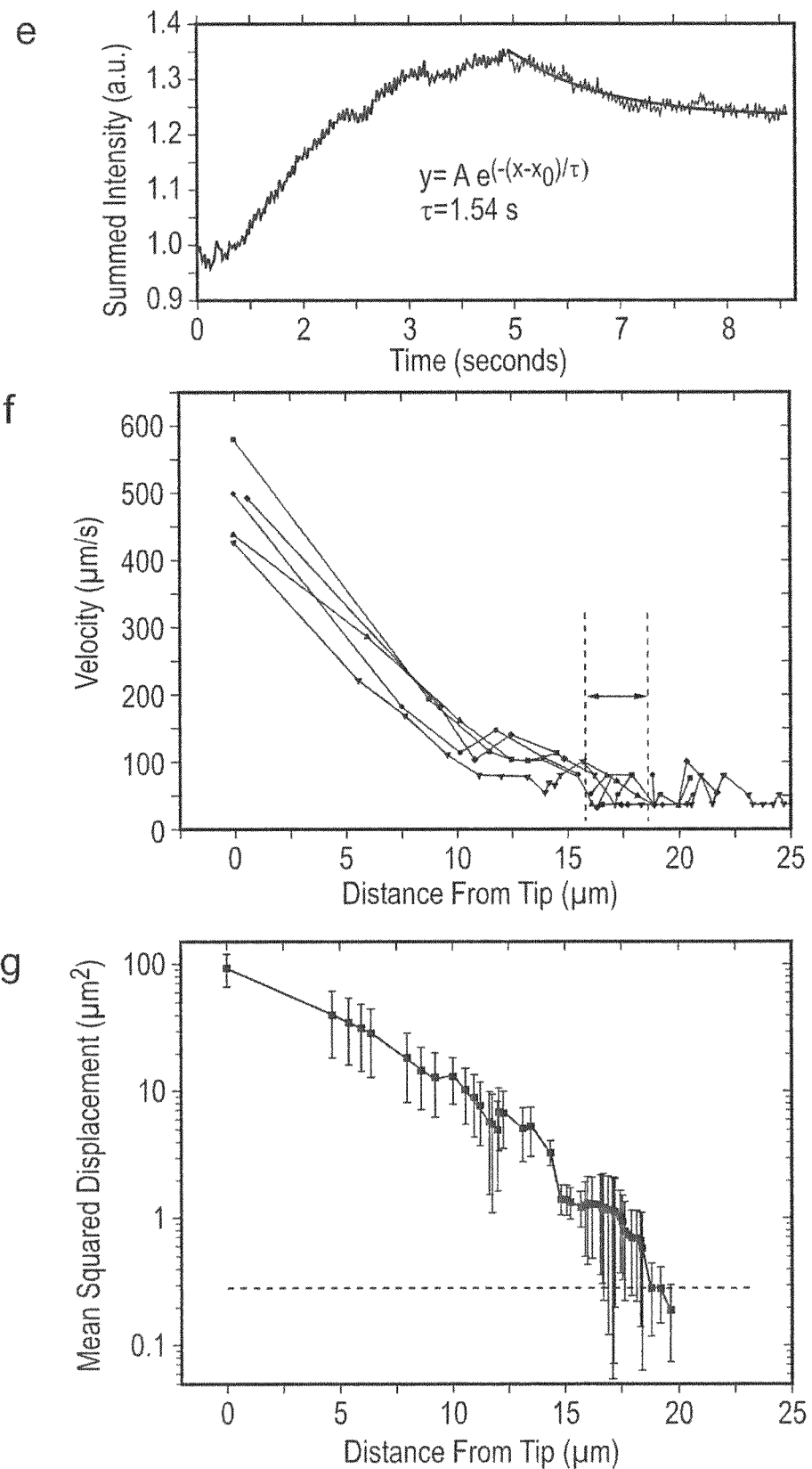

FIG. 3 shows fluorescence-based imaging and analysis of YOYO-labelled DNA trapped at the tip of a nanopipette. In particular, FIG. 3 illustrates:
   (a) YOYO-labelled 10 kbp DNA sample with the gold-coated nanopipette positioned 50 µm above the surface of the planar counter electrode with both electrodes grounded.
   (b) YOYO-labelled 10 kbp DNA sample with an AC voltage being applied between the gold-layer on the nanopipette and the counter electrode.
   (c) Still images showing the progression of DNA trapping which occurs at the tip of the nanopipette.
   (d) Image analysis performed on video recordings of DNA trapping conducted at various frequencies (1, 2, 3, 4 MHz).
   (e) Fitting the reduction of fluorescent intensity to an exponential ($\tau_{decay}=1.54$ s) for the 1 MHz condition. (f) DNA velocity profiles for five 10 kbp DNA molecules being trapped using the following conditions: $V_{pp}=12V$, $f_{AC}=1$ MHz.
   (g) Average mean squared displacement (MSD) of 10 kbp DNA as they transition into the trapping volume. Black dotted line: MSD expected for diffusion alone.

DEP trapping of DNA was observed optically using YOYO-labelled 10 kbp DNA. Upon applying an AC field to the gold electrodes, DNA was immediately drawn towards the tip of the nanopipette with a velocity which increased as the distance between the DNA and the tip became smaller. In the fluorescence-based measurement, a constant AC field was applied to a nanopipette filled with the same buffer used in translocation recordings. The filling of the pipette with buffer does not affect the DEP forces since the gold electrode and the maximum field gradients exist just outside the nanopipette's tip.

Although the DNA concentration was not critical to observing DEP trapping, at picomolar concentrations the DNA would be drawn towards the tip and become photobleached before the fluorescence intensity could be quantified. Using a DNA concentration of 10 nM, the DNA would aggregate at the tip at a rate sufficient to quantify the florescence as a function of frequency (FIG. 3a-d). Qualitatively, once the AC field was turned on the DNA would localize at the very end of the nanopipette as expected from simulations. As the trapping field was kept on for longer time periods, the fluorescent region around the tip would grow in size due to the accumulation of labelled DNA. The DNA aggregate at the tip grows in size since the DEP trapping forces are still high enough to cause additional DNA to be drawn towards the tip but steric exclusion restricts further motion towards the tip.

For these experiments the tip of the nanopipette was lowered to 50 µm from the gold-coated surface and an AC potential, of various frequencies, were applied to the two gold electrodes. We would expect the DEP forces to decrease in magnitude as the AC frequency is increased since the CM factor is sigmoidal-shaped as a function of frequency. Indeed we observe the highest fluorescence intensity for the 1 MHz condition which maximizes at about 4.5 seconds after applying the AC field. Interestingly, we see a decrease in the intensity past this point which is likely due to the DNA closest to the tip (trapped within the focal plane for the most time) being photobleached. Other scenarios that would explain the decreased fluorescence after 4.5 seconds (for the 1 MHz condition) would include variations in the DEP force or the sudden introduction of electrokinetic flow. Both are unlikely scenarios considering the timescale of onset (i.e. 4.5 s). Furthermore, the decrease in fluorescence intensity follows an exponential decay (FIG. 3e) which is a characteristic trend observed for photobleaching.

In order to characterize the DEP forces acting on the DNA, the spatial position of the DNA relative to the tip was tracked using image processing. As the DNA diffuses close to the tip (15-20 µm) the velocity of the DNA increases linearly (constant acceleration) due the DEP trapping force (DNA trajectories plotted in FIG. 3f). The mean squared displacement (MSD) of DNA was calculated using the 2D diffusion equation ($<x^2>=4Dt$) since the optical images represent a projection of the fluorescence into a 2D image. The MSD was averaged over two frames (15 ms per frame) and plotted against the MSD expected for diffusion alone (FIG. 3g; $D_{10\ kbp\ DNA}=1.05\times10^8$ cm$^2$/s)$^{17}$. The point where DNA crosses over from a diffusion-limited regime to a DEP regime occurred between 16 and 19 μm from the tip (marked by arrows in FIG. 3f). Based on our simulations, the trapping radius is significantly smaller than the 16-19 μm found experimentally leading us to believe that other sources of flow could be bringing DNA into the trapping volume. The corresponding volume where DNA molecules are being trapped from can be approximated by assuming the trapping volume is a sphere and subtracting the volume of a cone (i.e. the space occupied by the pipette) leading to a trapping volume of 17,153-28,724 μm$^3$ (details of calculation supplied in Supporting Information).

Electrical Measurements

The ionic current was measured using an AxoPatch 200B patch-clamp amplifier (Molecular Devices, USA) in voltage clamp mode. The signal was filtered using a low-pass filter at 10 kHz and digitized with a Digidata 1440 at a rate of 111 kHz and recorded using WINWCP software. WINWCP was used instead of pClamp because it allowed for synchronized triggering of both the AC and DC components. Data analysis was carried out using a custom-written MATLAB analysis routine. The baseline current was calculated via moving window for every data point. Event widths (dwell time) was obtained by measuring the full-width-half-max (FWHM) of the current reduction. Current drop was calculated as current peak maximum after subtraction of the baseline current.

Figure 4:
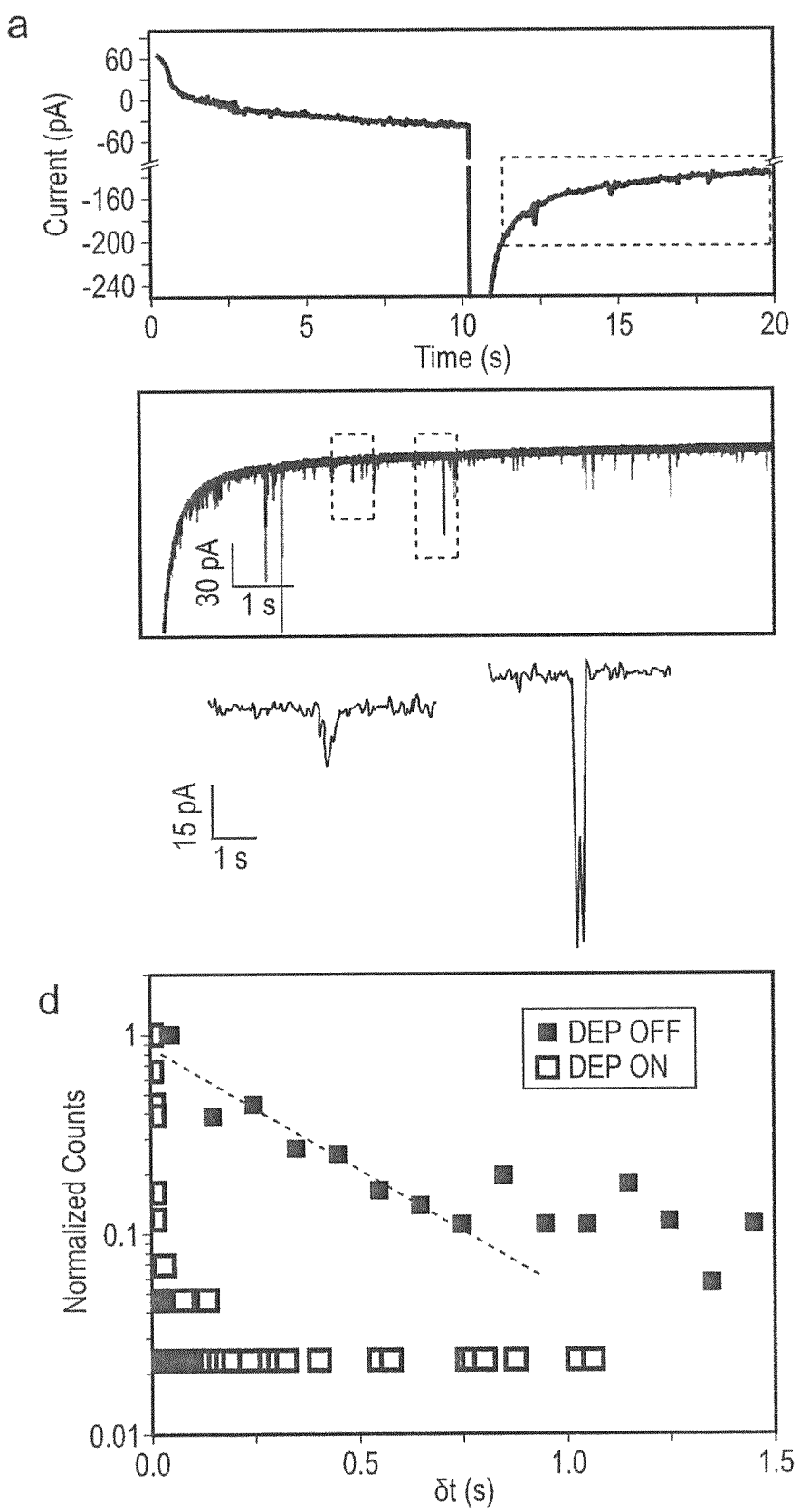
Figure 4:
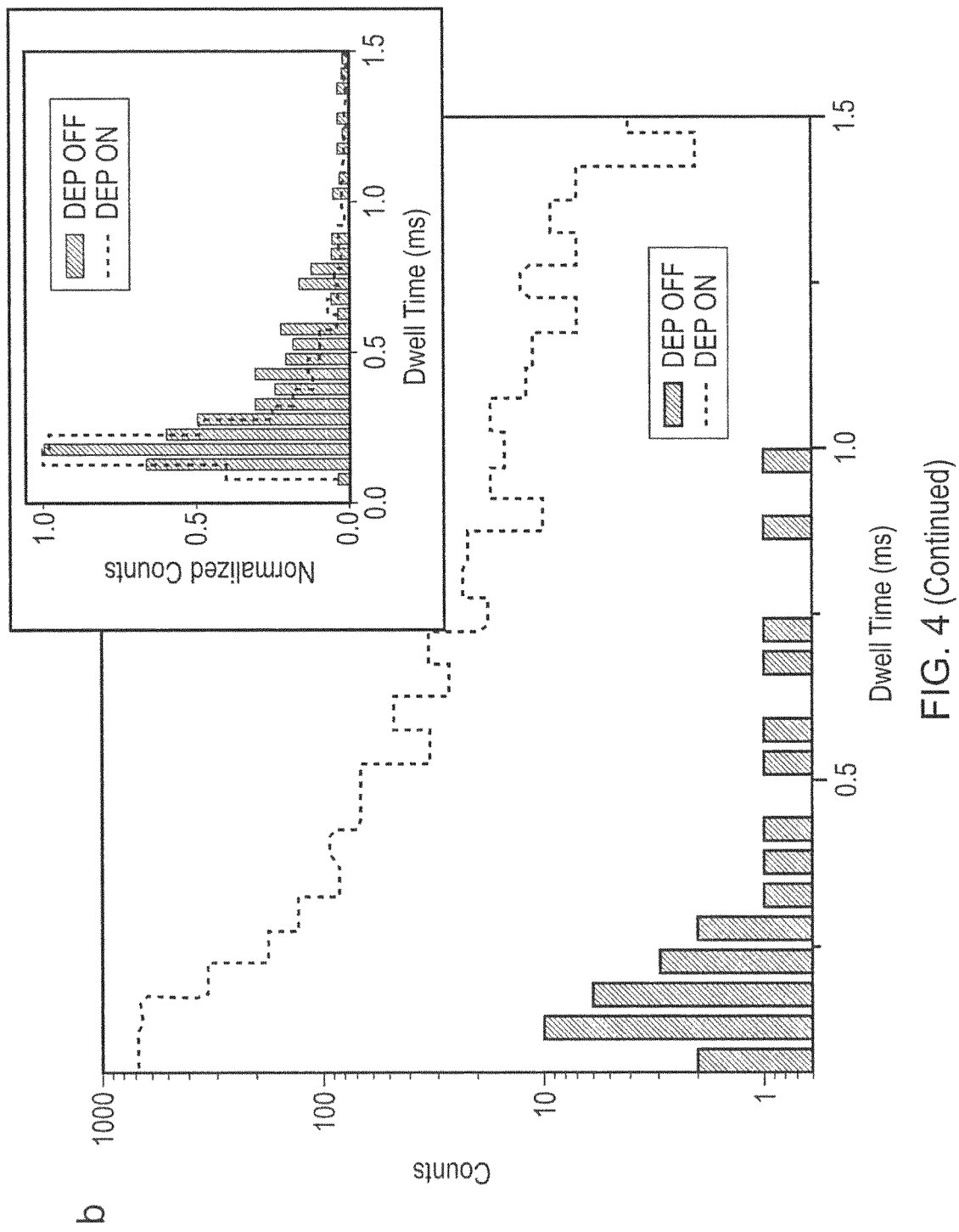
Figure 4:
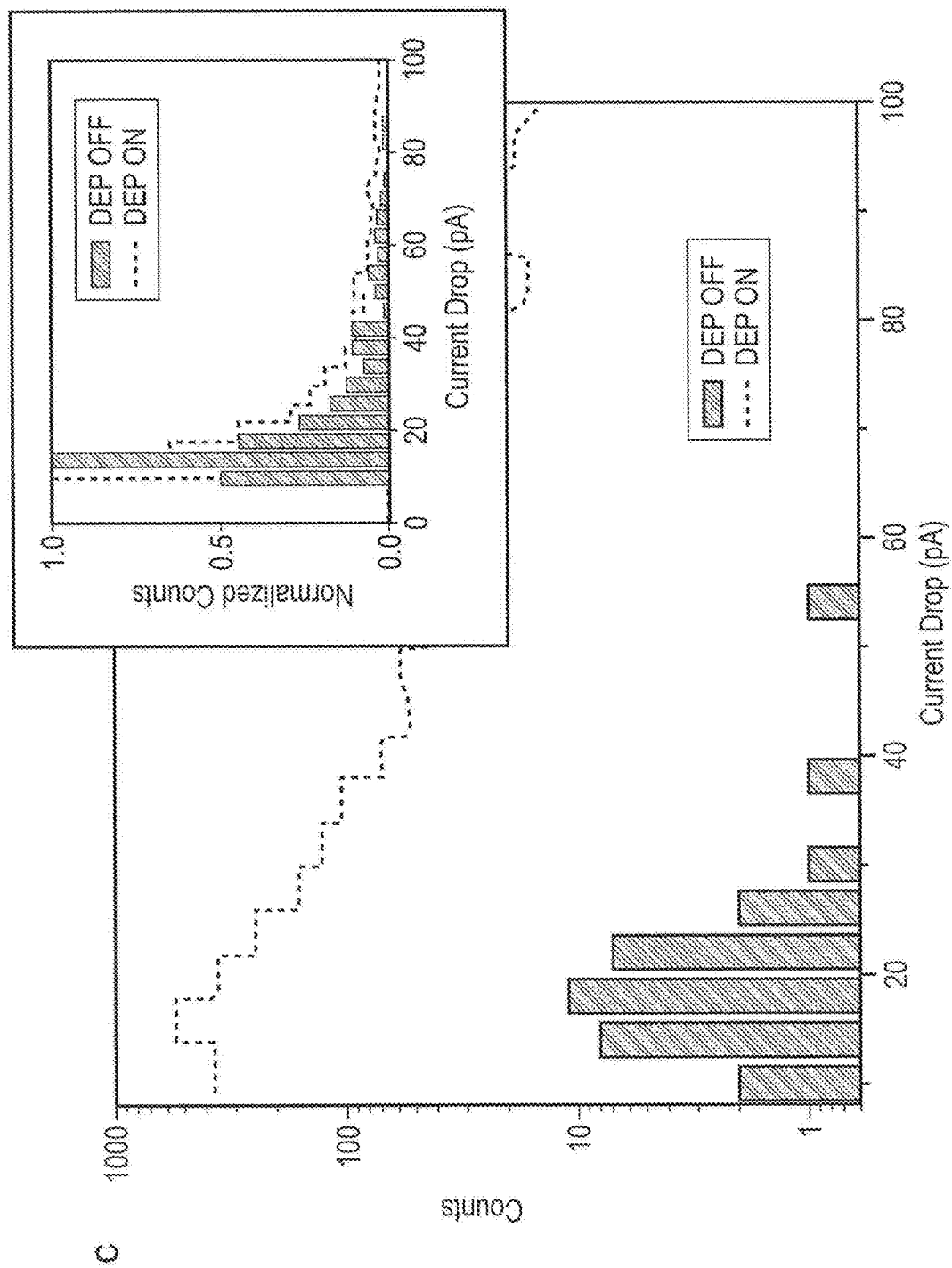
Figure 4:
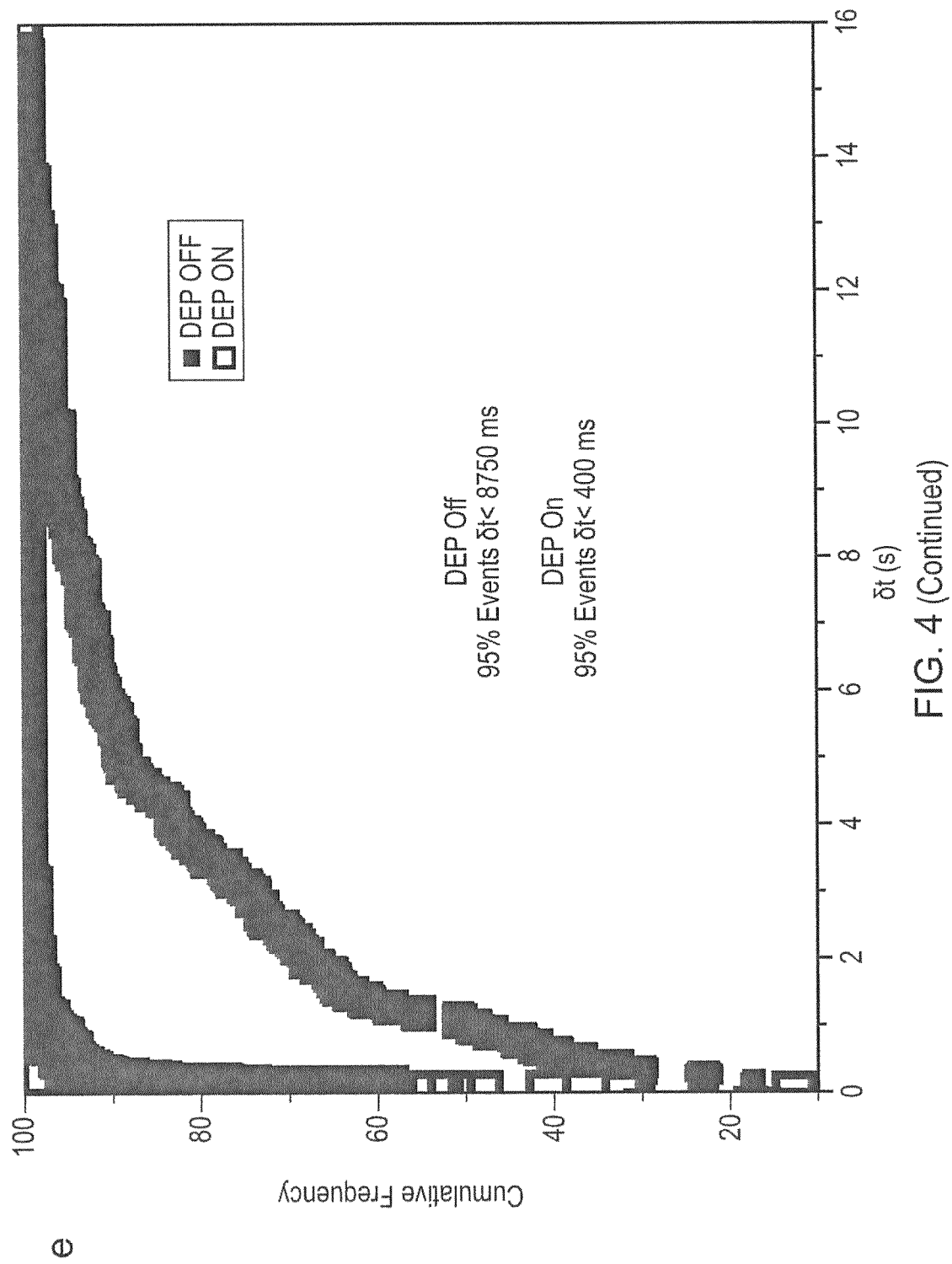

FIG. 4 shows event analysis of translocation events acquired through DEP-based pre-concentration. In particular, FIG. 4 illustrates:

(a) Current traces of a typical stimulation/recording cycle with various time scaling. The first ten seconds is the pre-concentration phase and the later ten seconds is the translocation recording phase. The lower panel shows typical events representing a single DNA molecule translocation (~96% of events), as well as a DNA aggregate translocating the pore (~4% of events).

(b) Time-normalized histogram of the dwell time comparing translocations with and without DEP pre-concentration. Inset: count-normalized distributions with and without DEP pre-concentration.

(c) Time-normalized histogram of the current drop comparing translocations with and without DEP pre-concentration. Inset: count-normalized distributions with and without DEP pre-concentration.

(d) Normalized histogram of the inter-event time (δt) with and without DEP pre-concentration.

(e) Cumulative frequency plot of the inter-event time (δt).

Prior to DEP trapping experiments, the conditions for electrically sensing DNA were optimized and tested using gold-modified nanopipettes. In these preliminary experiments we did not control the distance between the tip and the surface and a voltage-dependent analysis of the translocation kinetics was conducted (results supplied in the Supporting Information). In summary, we found that the optimal conditions for DNA sensing required a voltage bias, |ΔV|, of 500 mV which was used throughout the rest of the experiments. After independently optimizing DEP and DNA sensing protocols, both methods were combined together in sequence (10 seconds of DEP trapping followed by 10 seconds of ionic current measurements under a DC bias). In most instances, applying an AC voltage to the outside of the pipette still allowed for the measurement of ionic current with limited noise increases as long as the applied frequency (typically in the MHz regime) was higher than the filter frequency (10 kHz) for the recording (Supporting Information). This observation is exciting due to the possibility of applying both AC and DC fields to different components of the nanopipette allowing one to apply two independent forces to the DNA molecule with the goal of slowing down the translocation time; a major issue still to be solved by next generation nanopore DNA sequencers.

Once the AC field was turned off and the DC field was turned on, capacitance led to a transient spike in current which leveled off within 1 second while the earliest possible event could be detected within 200-300 milliseconds. Although we expect to miss translocation events during this time, we discovered that DNA translocation rate enhancement is maintained well past this transient period. It should be pointed out that the capacitance effects are only observed due to the DC field which is applied across the pore. In experiments where the AC field was simply turned off and no DC field was applied, the ionic current would immediately reach a steady ionic current with no transient capacitance.

Using a DNA (10 kbp) concentration of 500 pM, DEP trapping and subsequent DNA translocations were performed. While ionic current was measured through the pore throughout the 20-second recording time, DNA was detected only in last 10 seconds when a DC voltage is applied to the Ag/AgCl electrodes (|ΔV|=500 mV). The dwell time of the DNA was measured as the full width half maximum (FWHM) of the ionic current signature for each translocation event. These values were then tabulated and plotted as a histogram along with data obtained without DEP trapping (FIG. 4b). The data was time-normalized (recording time=180 s) and plotted on a log scale to show both populations (linearly scaled plots are shown in the Supporting Information). The number of events detected while using DEP to pre-concentrate the DNA was 2715 while without trapping resulted in only 34 events. Importantly, translocation events are not affected by the DEP trapping as shown by a count-normalized histogram (FIG. 4b (inset); n=2315 events for no trapping condition). Similarly, the maximum current drop obtained for each event was tabulated and plotted as a log scale histogram (time-normalized) and a linearly scaled histogram (count-normalized) (FIG. 4c). A voltage-dependent study of how the current drop and dwell time distributions change between 400 and 700 mV can be found in the Supporting Information.

The inter-event time (δt) was extracted from the data by taking the difference between the start times of two consecutive events. The δt parameter has an exponential distribution which can be fitted by a linear curve on a log scaled axis (as shown in FIG. 4d). Most notable however is that the δt values during experiments where DEP trapping was used show a marked decrease. This is expected since there are more events per unit time due to the pre-concentration effects of DEP. Alternatively, a cumulative histogram can be used to show the percentage of events which occur below a certain inter-event time. Comparing between experiments with and without DEP trapping, we observed that 95% of inter-event times were below 8750 ms when trapping was not used while the same number of events occurred below 400 ms with trapping forces being used to pre-concentrate the DNA.

Figure 5:
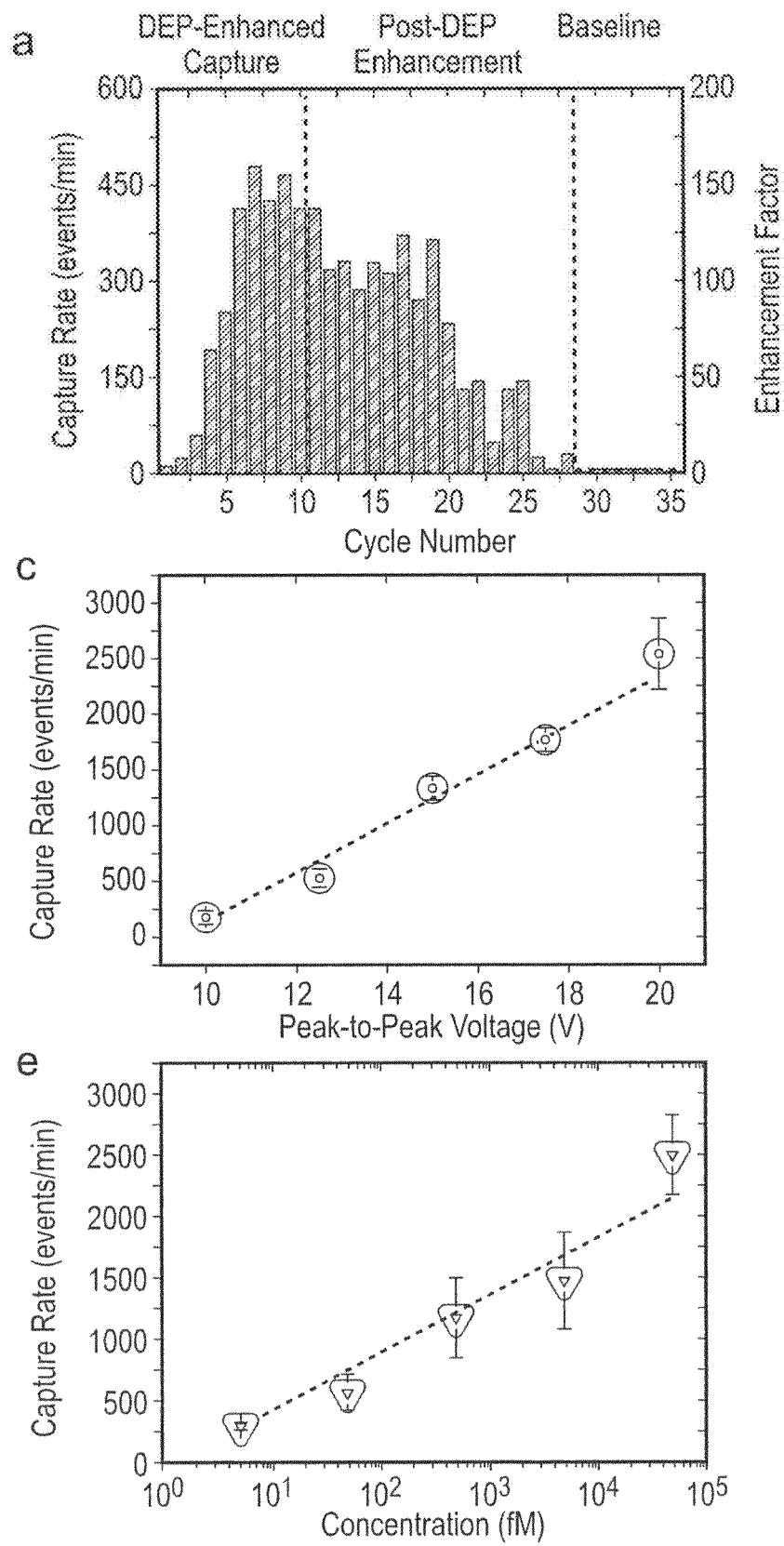
Figure 5:
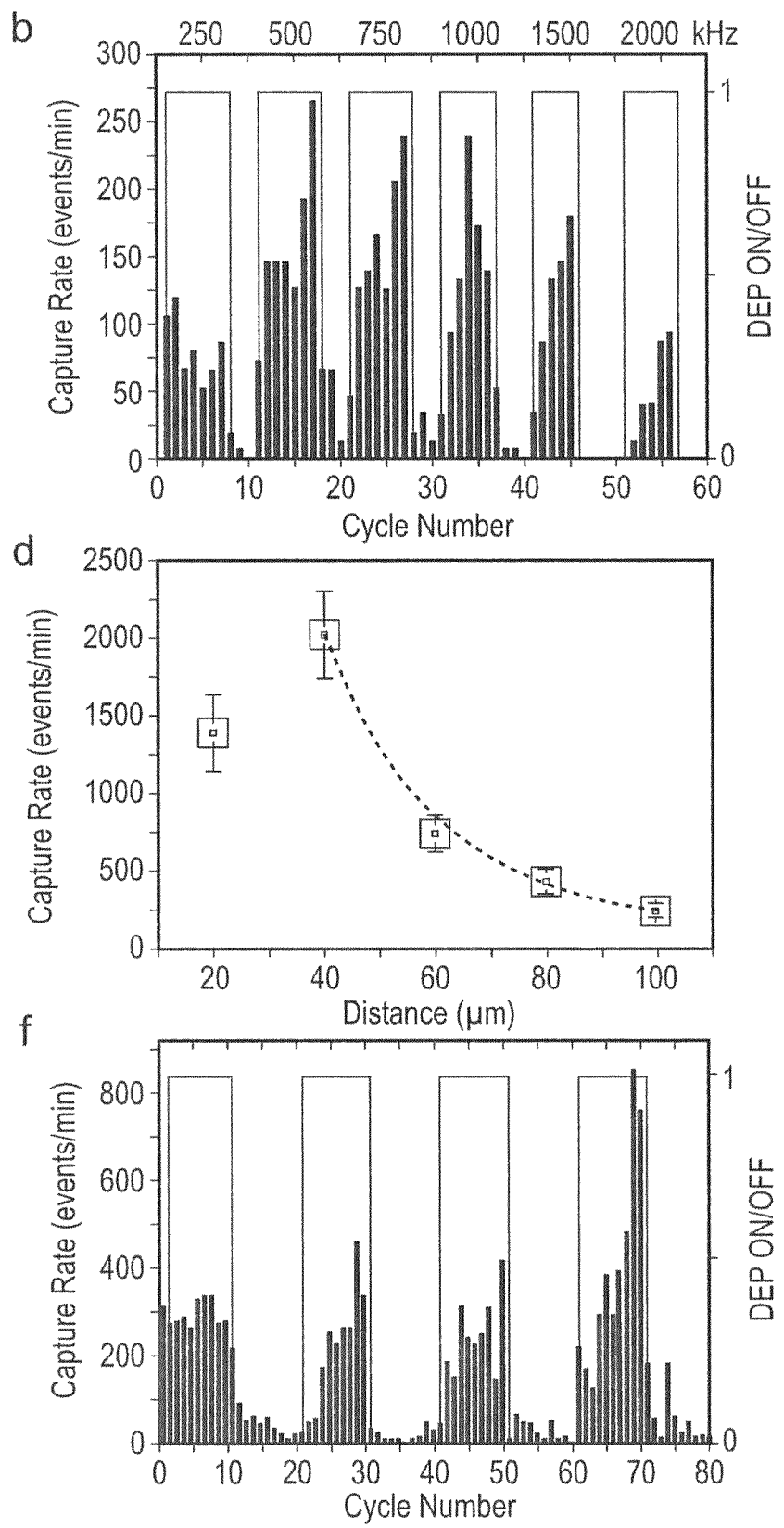
Figure 5:
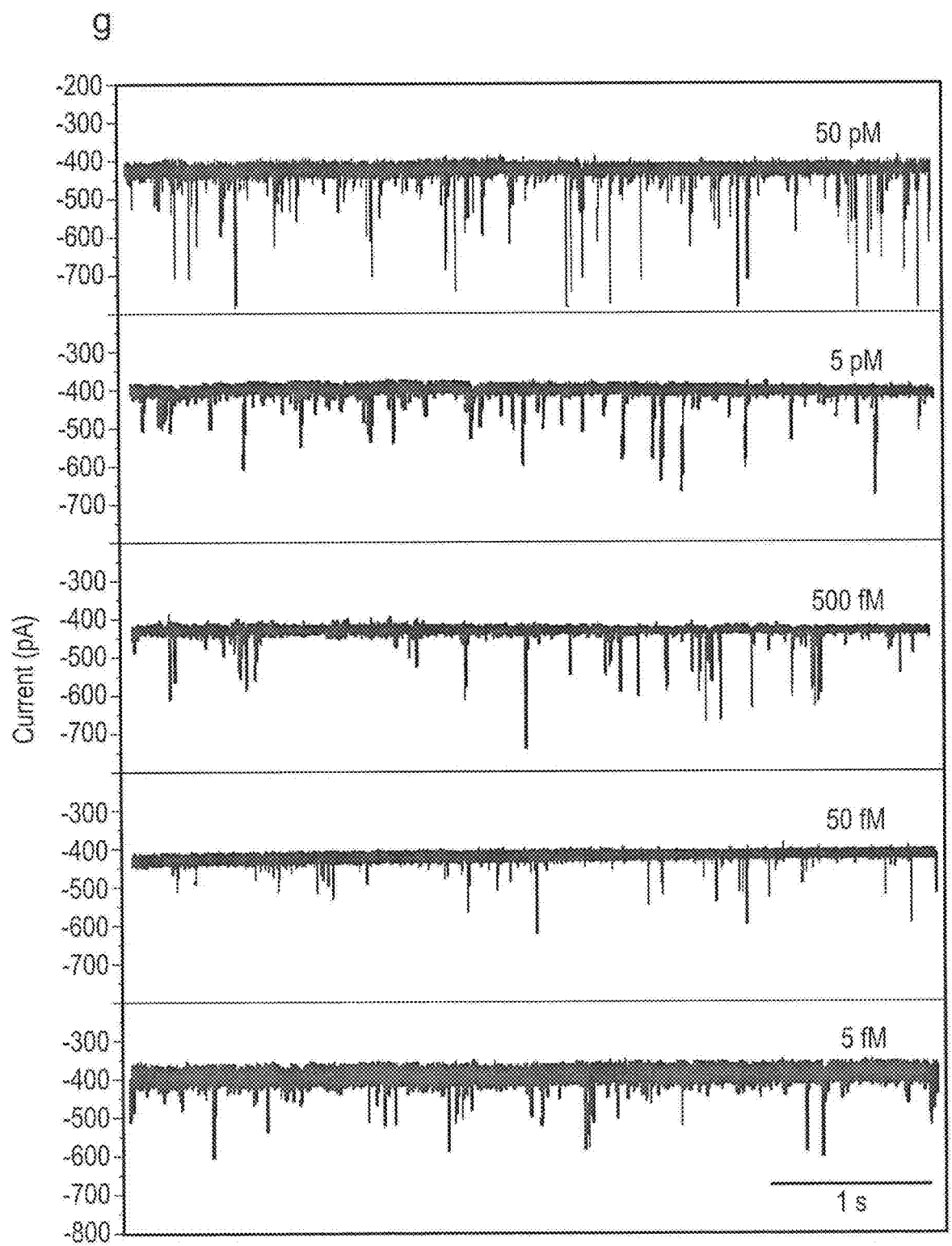

FIG. 5 shows DEP capture rate analysis. In particular, FIG. 5 illustrates:

(a) Capture rate per recording cycle where each recording cycle was 10 s in duration. The first 10 cycles were performed with 10 s of DEP pre-concentration whereas the last 25 cycles were proceeded by 10 s of no trapping forces.

(b) Capture rate per recording cycle where DEP pre-concentration was turned on/off. The DEP trapping frequency was also increased with each subsequent DEP pre-concentration phase.

(c) Capture rate as a function of the peak-to-peak voltage used for the DEP trapping.

(d) Capture rate as a function of the nanopipette tip-counter electrode gap distance.

(e) Capture rate as a function of the 10 kbp DNA concentration.

(f) Capture rate per recording cycle for a 5 fM DNA sample where DEP pre-concentration was turned on and off for 4 consecutive cycles.

(g) Current traces obtained using DEP as a pre-concentration step for five different concentrations (50 pM, 5 pM, 500 fM, 50 fM, and 5 fM). A bias of $|\Delta V|=500$ mV was applied across the nanopore for all experiments.

In order to characterize the efficiency of trapping in terms of the measurable quantity of DNA passing from one side of the pore to another, the capture rate was calculated as the number of events per unit time. As stated before, ten seconds of trapping (12 $V_{pp}$, 1 MHz) was followed by ten seconds of translocation recording performed at $|\Delta V|=500$ mV. The typical trend that was observed in all experiments was that the first cycle of trapping/translocation (1 cycle=10 s trapping+10 s translocations) yielded an increase in capture rate which was followed by further enhancement with each subsequent cycle and saturated after 6-7 cycles. In fact the trend shows an exponential increase in capture rate as a function of cycle number (FIG. 5a) up until the 7$^{th}$ cycle. If we assume each cycle is modelled as a rate balance ($R_{in}$−$R_{out}$=$R_{acc}$) where the input of mass (i.e. DNA) is governed by DEP and the output of mass is governed by the electrophoretic transport of DNA through the pipette, we can justify the increase in capture rate across cycles, $R_{acc}$, as the result of an imbalance between these two rates. The accumulation of DNA at the tip therefore seems to be a key contributor to the enhancement observed in our experiments. In fact we observed enhanced capture rates that extended 5 minutes after a DEP cycle was employed.

If we assume DNA is located close to the nanopore during a DEP cycle, then the timescale in which DNA could be re-captured by the DC potential depends on how far diffusion can displace the DNA after the AC voltage is turned off. The recapturing of DNA using biphasic voltage pulses was shown previously by Gershow and colleagues[18]. In this study DNA could be recaptured after a 32 ms delay period with a probability of ~0.4. Despite the fact that this study kept a +120 mV potential applied to the pore which would actively drive DNA away from the pore during the delay period (whereas this study applied no potential to the pore post-DEP trapping) we still expect that diffusion would displace the DNA sufficiently far from the tip within a few seconds. If we assume the capture radius during DC field-driven translocations is 3 μm from the pore, then we should expect DNA to diffuse out of the capture radius in 2.14 s, (calculated using the equation for mean squared displacement) which is much shorter than the >8 minutes (20 s×25 cycles=8.3 min.) of enhancement observed here. In order to explain the post-DEP enhancement observed in FIG. 5a, we suggest that DNA becomes adsorbed onto the gold surface during DEP trapping and randomly desorbs over time. The maximum capture rate occurred after seven cycles where DEP was used to pre-concentrate the DNA and an enhancement factor observed over the baseline capture rate was 160.

By reducing the peak-to-peak voltage used for DEP trapping (20 to 10 V), the timescale for post-DEP enhancement was effectively reduced so that within two cycles of DEP not being employed, the capture rate fell to near-baseline values. The lack of significant capture rate enhancement after DEP pre-concentration was removed signifies that the DNA accumulation term was reduced and most of the DNA captured by DEP was removed by translocating the DNA through the pore. Cycles where DNA pre-concentration was used can clearly be identified from the capture rate data (FIG. 5b) where various AC frequencies were used in combination with a DC voltage of $|\Delta V|=500$ mV.

Typical AC frequencies ($f_{AC}$) and voltages ($V_{pp}$) used for DNA trapping range from $f_{AC}$=100 kHz–2 MHz and $V_{pp}$=8-20 V. Working within this range, we characterized the capture rate post-DEP trapping using our nanopipette devices. In analyzing the data presented in FIG. 5c-e, ten DEP pre-concentrating cycles were used and each data point represents the average of the last 5 cycles. As $V_{pp}$ was increased from 10 V to 20 V, we observed a linear increase in the capture rate (distance between electrodes=20 μm). Surprisingly, while $V_{pp}$ was only doubled at the extreme ends of the values tested (10 V and 20 V), we observed a 10-fold increase in the capture rate. The larger than expected voltage dependence may stem from the fact that the threshold for DNA attraction during the DEP phase of the cycle is achieved further up from the shaft of the pipette. The trapping volume would therefore increase at the tip as expected for a DEP hotspot, while DNA close to the gold surface upstream from the tip is also funneled towards the tip. Due to the geometry of the nanopipette, we expect trapping occurs over a larger area as well as extends further from the tip when $V_{pp}$ is increased.

The distance between the nanopipette tip and the gold-coated surface of a slide was determined by simultaneously measuring the resistance between the gold surface and the gold on the nanopipette as well as conductance through the pore using the Ag/AgCl electrodes. When the tip of the pipette contacted the surface, the resistance between the gold electrodes instantaneously dropped from 18 MΩ to 0.3 kΩ. Due to the change in ionic concentration at the gold surface, a corresponding spike in ionic conductance through the pore was also observed which was completely reversible indicating that the nanopore size was not altered (see Supporting Information). A full schematic of the system and protocols used to position the nanopipette various distances from the surface can be found in the Supporting Information.

Upon positioning the tip of the pipette at the surface of the gold-coated slide, the nanopipette was lifted in 20 μm steps and DEP/translocation cycles were recorded for each position. As the gap between the two gold electrodes became smaller, the capture rate increased most significantly between 100 μm and 40 μm. Interestingly, at 20 μm the capture rate was reduced slightly. Based on the trapping volume data obtained using YOYO-labelled DNA described earlier, 20 μm is on the same scale as the distance away from the tip where DNA begins to respond to DEP forces. It is likely that the decrease in capture rate is therefore due to the trapping volume being geometrically confined by the surface of the gold-coated slide. Other effects related to a surface being in close proximity to the trapping volume may also be responsible for the decrease we observe.

Using a tip-to-surface gap distance of 20 μm and optimized DEP trapping conditions (20 $V_{pp}$ and 1 MHz), the concentration of DNA was reduced from 500 pM to 5 fM.

The capture rate logarithmically decreases as a function of bulk concentration (FIG. 5e). Although sub-pM DNA concentrations are typically not capable of being sensed using nanopores, DEP pre-concentration allowed the full range of fM concentrations to be detected. Previous studies which used salt gradients, and later using controlled DNA delivery methods, showed the ability to enhance the capture rate of DNA down to ~3 pM. Both of the previous methods rely on the electrophoretic properties of DNA to enhance the capture radius and the local concentration, respectively. DEP-based methods, which use the polarizability of DNA, are shown here to be a much more powerful method for enhancing the capture rate of DNA. At the 3 fM DNA concentration, a capture rate of 315±147 events/min is achieved. Prior to experiments, a DC bias was applied to the same pipette for 2 minutes with <5 events being detected. The current traces at each DNA concentration show that more DNA being trapped at the tip typically results in DNA aggregates being formed and translocated. However at 5 fM the formation of DNA aggregates at the tip was significantly reduced leading us to believe that DNA had a lower local concentration around the tip prior to translocation.

CONCLUSION

Nanopipettes offer several advantages over membrane-fabricated solid-state nanopores. Aside from requiring less sophisticated instrumentation and drilling procedures, nanopipettes can easily achieve single molecule delivery into microfluidic droplets or living cells thereby broadening the applications of nanopore technology. We have demonstrated the use of metallized nanopipettes, and more generally nanopores, for DEP trapping and DNA pre-concentration. We have shown the ability of an implementation of the apparatus to sense DNA at a concentration of 5 fM at an event rate of 315 events/min. We conclude based on optical studies that the trapping radius is ~18 μm which is significantly larger than the capture radius obtained by traditional electrophoretic-based capture mechanisms. The proposed DEP-based method of preconcentrating an analyte could also be extended to other spectroscopies including SERS. Lastly, combining AC and DC fields may further provide a method to slow down the DNA by applying two independent forces to the translocating DNA.

Dual-Nanoelectrode Structure

A dual-nanoelectrode structure has also been developed to address such problems. Implementations of such a system may enable relatively fast, inexpensive and reliable label-free in-flow separation and detection of analytes with single molecule resolution. Also disclosed below is a method for forming such a structure. Previously, the technological challenges associated with forming suitable structures using prior art techniques rendered difficult or impracticable the application of dielectrophoresis to single molecule detection.

Figure 6A:
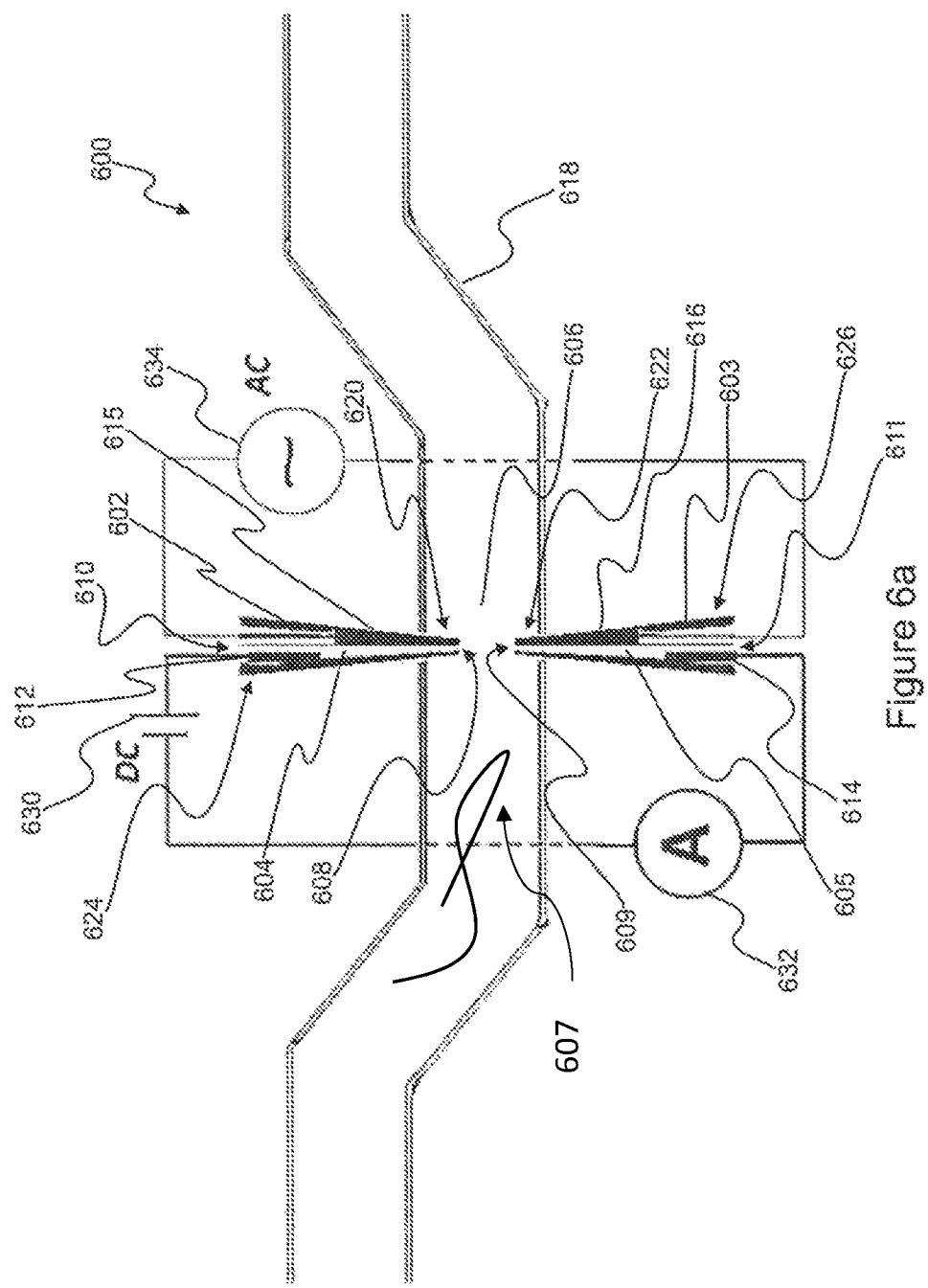
FIGS. 6a to 6d illustrate views of a further apparatus for concentrating polarizable molecules within a fluid medium.
Figure 6B:
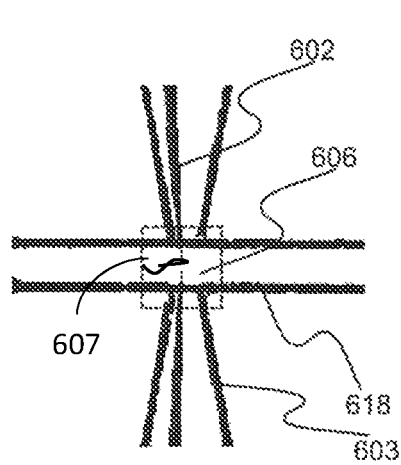
Figure 6C:
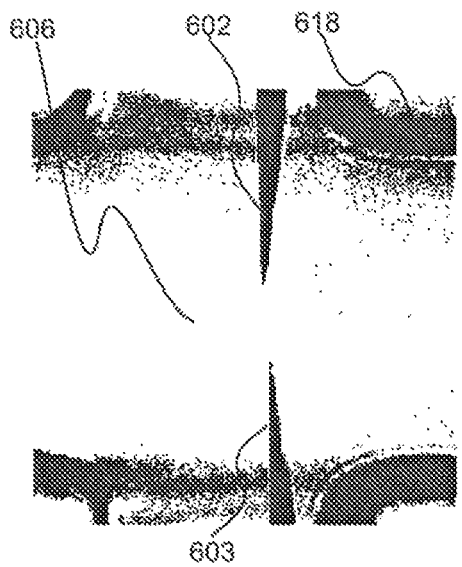
Figure 6D:
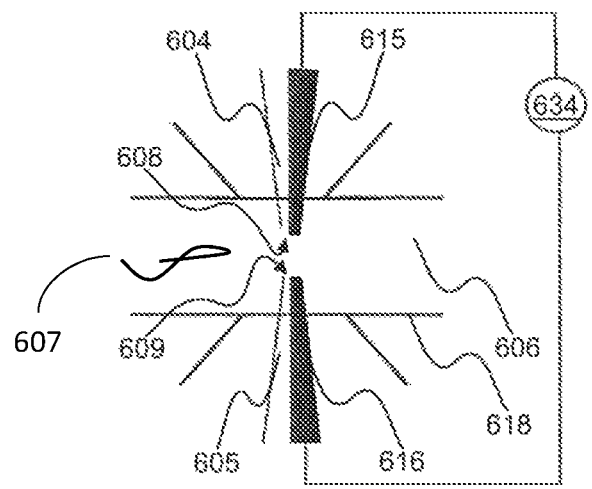

FIGS. 6a to 6d illustrate views of a further apparatus for concentrating polarizable molecules within a fluid medium. FIGS. 6a and 6d illustrate schematic views representing the apparatus 600. FIGS. 6b and 6c illustrate micrographs of an implementation of the apparatus 600.

The apparatus 600 comprises a first pipette 602 and a second pipette 603 and a fluid tube 618. The fluid tube 618 may be provided by a microfluidic channel with a diameter of, for example, 100 μm. Each pipette has a proximal end 620, 622 and a distal end 624, 626. The proximal end 620, 622 of each pipette 602, 603 tapers such that the end of each pipette 602, 603 has a radius of between 20 nm and 1 μm.

The proximal ends 620, 622 of the pipettes 602, 603 are disposed within the fluid tube 618. In this example, the first pipette 602 extends from a side wall of the fluid tube that opposes a side wall from which the second pipette 603 extends. In this way, the proximal end 620 of the first pipette 602 faces the proximal end 622 of the second pipette 603. The proximal end 620 of the first pipette 602 may be spaced between 5 μm and 30 μm from the proximal end 622 of the second pipette 603. A reservoir 606 of fluid may be considered to be provided within the fluid tube 618 adjacent to the proximal ends 620, 622 of the pipettes 602, 603. The fluid in the reservoir 606 may be a solution similar to that described previously with reference to FIG. 1. Analyte flow along the fluid tube 618 may be established by connecting the fluid tube 618 to an external analyte reservoir mounted on a syringe pump using, for example, a Teflon tubing.

Each pipette 602, 603 defines a cavity 604, 605 that extends between the proximal end 620, 622 and the distal end 624, 626 of the respective pipette 602, 603. The cavities 604, 605 define a flow path for fluid along the pipettes 602, 603. Depending on the polarity of a signal applied, each of the proximal apertures 608, 609 at the proximal ends 620, 622 of the first and second pipette 602, 603 may be referred to as an upstream aperture or downstream aperture, and each of the distal apertures 610, 611 of the cavities 604, 605, at the distal ends 624, 626 of the pipettes 602, 603 may be referred to as an upstream aperture or downstream aperture.

The size of the apertures 608, 609 is such that molecules from the fluid can pass into the cavity 604. The proximal apertures 608, 609 have a cross-sectional dimension of 200 nm. In some examples, the proximal apertures 608, 609 may have a cross-sectional dimension of less than 30 nm, or even less than 3 nm. The cavities 604, 605 may be considered to be nanopores due to their nano-scale dimensions.

First and second translocation electrodes 612, 614 are positioned relative to the pipettes 602, 603 to enable generation of a direct current (DC), or non-time-varying, electric field passing through the cavity. The first translocation electrode 612 is provided by the first pipette 602 and the second translocation electrode 614 is provided by the second pipette 603. Optionally, the translocation electrodes 612, 614 are provided within the cavities 604, 605, but do not completely occlude the cavities 604, 605. Each translocation electrodes 612, 614 may comprise a metal or metallic conductor, or a carbon deposit. For example, the translocation electrodes 612, 614 may be Ag/AgCl quasi-reference counter electrodes. The apparatus 600 may further comprise a DC voltage source 630 coupled to the respective translocation electrodes 612, 614. The translocation electrodes 612, 614 may be considered to generate a translocation field when in use. That is, an electric field that is configured to draw molecules 607 from the fluid in the reservoir 606 through the proximal aperture 608 of the cavity 604, through the cavity and, optionally, through the distal end 610 of the cavity 604. In order to provide this functionality, first and second translocation electrode 612, 614 may be provided adjacent to respective distal ends 624, 626 of the pipettes 602, 603 in order to maximize the distance over which the translocation electrodes can accelerate molecules within the fluid. In such examples, the first and second translocation electrodes 612, 614 are provided on opposing sides of the reservoir 606.

As well as providing an electromotive force to the fluid, the translocation electrodes 612, 614 may also be used to measure an ionic current of fluid within the cavity 604 using, for example, an ammeter 632. The partial occlusion of the cavity by the presence of a molecule within the fluid may be signaled by a reduction in the current measured between the translocation electrodes 612, 614, as discussed previously with reference to FIG. 1.

The apparatus also comprises first and second trapping electrodes 615, 616. The first and second trapping electrodes 615, 616 are provided at, or adjacent to, the proximal apertures 608, 609 of the respective pipette 602, 603. The first and second trapping electrodes 615, 616 may be provided by a carbon deposition within the pipettes 602, 603. The first and second trapping electrodes do not necessarily prevent the passage of fluid through the cavity 604, 605 of the pipette 602, 603. The trapping electrodes 615, 616 in this example are therefore provided on opposing sides of fluid within the reservoir 606. In this way, the trapping electrodes 615, 616 are positioned relative to the pipettes 602, 603 to enable generation of an inhomogeneous or non-uniform electric field adjacent to the proximal apertures 608, 609 on the application of a time-varying voltage. The trapping electrodes 615, 616 may be considered to generate a dielectrophoretic field when in use. The trapping electrodes 615, 616 may therefore also be described as dielectrophoresis (DEP) electrodes. The apparatus may further comprise an AC voltage source 634 coupled to the trapping electrodes 615, 616. A controller such as that described previously with reference to FIG. 1 may also be used with the apparatus 600 of FIG. 6.

An increased concentration of a target analyte around the dual-nanoelectrode probes may be achieved by generating a dielectrophoretic field across the two trapping electrodes 615, 616 while flowing a sample fluid containing the target analyte through the fluid tube 618. Analyte detection can either be performed along with concentration or post-concentration of the analyte by applying a potential bias across the two translocation electrodes 612, 614 and monitoring the ion current flowing between them. Variations in ion current recorded could serve as the signal for single molecule detection.

By using pipettes, which may be fabricated with nanoscale features at the proximal ends 620, 622, the apparatus may be used to generate a high DEP field. In some examples, the DEP force, $|\nabla|E|^2$ may be up to $10^{-24}$ $V^2$ $m^{-3}$. Such apparatus can enable in-line single molecule detection from very low concentrations fluids. The concentration and separation of molecules from a mixed sample including but not limited to nucleic acids such as DNA, RNA and PNA, proteins and nucleic acid-protein complexes may be achievable.

In some examples, each pipette 602, 603 defines a plurality of cavities that are separated from one another by respective barriers. In such examples, the translocation electrode 612, 614 of one of the pipettes 602, 603 may be provided in a different cavity of a particular pipette 602, 603 to the trapping electrodes 615, 616 of that pipette 602, 603. The separation of the pipette 602, 603 into a structure with a first cavity and a second cavity is described further below with reference to FIG. 7.

In some examples, only one of the first and second pipettes 602, 603 provides a proximal aperture 620, 622 and cavity 604, 605 for ion transport.

The apparatus 600 incorporating two dual-nanoelectrode probes may be fabricated using a two-step process, which may offer a simplified method of manufacture compared to previous methods.

Figure 7:
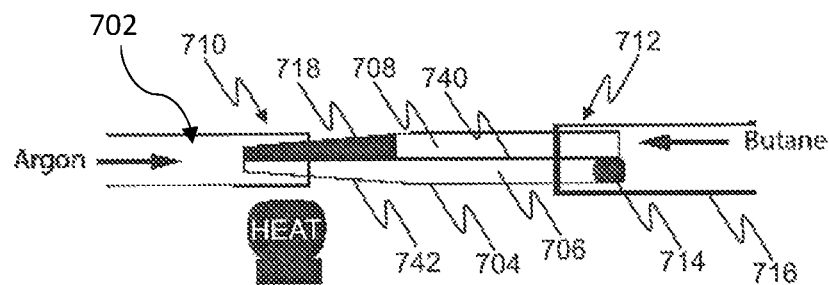
FIG. 7 illustrates a step in a method of forming a pipette for the apparatus of FIG. 6.

FIG. 7 illustrates the first step in a fabrication process for providing a pipette 704 for use in the apparatus of FIG. 6. In the first step, a quartz theta capillary (outer diameter 1.2 mm, inner diameter 0.90 mm, supplied by Friedrich & Dimmock, Inc) is pulled into a sharp point pipette 704 using a laser puller (P-2000, supplied by Sutter Instruments). The pipette 704 is double barreled, meaning that it defines a first cavity 706 and a second cavity 708. The first cavity 706 is separated from the second cavity 708 by a barrier that prevents fluid flow within the pipette 704 between the first cavity 706 and the second cavity 708. The first cavity 706, second cavity 708 and barrier 740 are all contained within the pipette by an outer wall 742. The pipette 704 also has a proximal end 710, adjacent to the point, nib or tip of the pipette 704, and a distal end 712 at the other extremity of the cavities 708, 710. The distal end 712 of the first cavity 706 is sealed using a sealant 714, such as Blu-Tack® (supplied by Bostik Ltd.). Tubing 716, which may be provided by a rubber tube, is secured around the distal end 712 of the pipette 704. A regulated flow of butane is passed from the tubing 716, through the distal end 712 of the pipette 704, through the second cavity 708 of the pipette 704, and subsequently out of the proximal end 710 of the pipette 704. An argon atmosphere is provided to the pipette 704 via a quartz theta capillary 702 at the proximal end 710 of the pipette 704. The tip at the proximal end 710 of the pipette 704 is heated using, for example, a butane torch. The heating is typically performed for 35 s, to pyrolytically deposit carbon 718 from the butane at the proximal end 710 of the pipette 704. The carbon 718 provides an electrode at the tip of the pipette 704.

In a second step, two of the fabricated dual-nanoelectrode probes are inserted into a pre-fabricated microfluidic channel (channel width of approximately 100 μm). The dual-nanoelectrode probes may be positioned face-to-face using a micromanipulator (supplied by Thor Labs) as described previously with reference to FIG. 6a to 6d. An inter-electrode gap (distance between proximal apertures of the two opposite dual-nanoelectrode probes) can be precisely varied from 2 μm to 100 μm by performing this procedure using an optical microscope with 60× water immersion objective lens. An electrical connection with the carbon electrodes in the dual-nanoelectrode probe may be established by inserting copper wires into the carbon filled barrel through the distal ends of the pipettes. In this way, the carbon electrode may be connected to a commercial function generator for generating a dielectrophoretic trapping field. The open barrels at the distal ends of the dual-nanoelectrode probe are filled with an electrolyte containing an Ag/AgCl quasi-reference counter electrodes. In this way, an ion current based nanopore single molecule detection system such as that described previously with reference to FIG. 6 can be formed.

Figure 8A:
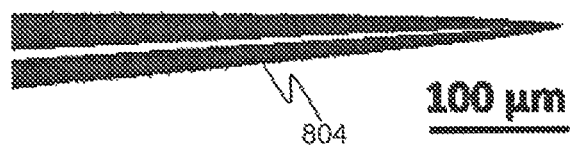
FIGS. 8a and 8b illustrate micrographs characterizing the pipette formed by the method of FIG. 7.
Figure 8B:
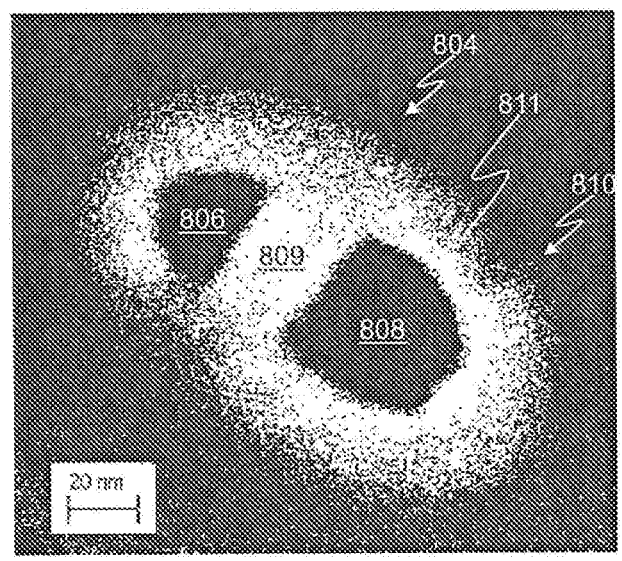

FIGS. 8a and 8b illustrate micrographs characterizing the structure formed in the first step of the fabrication process described with reference to FIG. 7. In FIG. 8a, a longitudinal view of the pipette 804 is shown. The pipette has an axial length greater than 100 μm. FIG. 8b illustrates an axial view of the proximal end 810 of the pipette 804. The pipette 804 has a first cavity 806 and a second cavity 808. The first cavity 806 is separated from the second cavity 808 by a barrier 809. The barrier 809 is formed of the same material as an external wall 811 of the pipette 804. Each of the first cavity 806, second cavity to 808 and barrier 809 have a width less than 200 nm. In the example shown, the first cavity 806 has a width of approximately 20 nm and the second cavity 808 has a width of approximately 40 nm. In other examples, the first cavity 806 may have a similar width to the second cavity 808.

The following description of the invention is also disclosed. It will be appreciated that the subject matter described in the statements below may be combined with that described elsewhere herein.

Statement 1: An apparatus for concentration of macromolecules in a solution, colloid or suspension comprising:
a cavity of up to 200 nm in dimension, preferably <25 nm;
at least electrodes connected on a DC field in order to carry out translocation of macromolecules through the cavity and analysis of the macromolecules; and
at least two electrodes (comprising at most one of the previously described electrodes) connected by an AC field whereby at least one is distinct from the cavity.

2. The apparatus of statement 1 wherein the cavity comprises a nanopore.

3. The apparatus of statement 2 wherein the nanopore is a solid-state nanopore, preferably silicon based.

4. The apparatus of statement 2 wherein the nanopore is biological.

5. the apparatus of statement 1 wherein the electrodes connected by DC field carry out DNA sequencing.

6. The apparatus of statement 1 wherein one or more of the electrode(s) connected by AC field is planar.

7. The apparatus of statement 6 wherein the planar electrode is located around the cavity.

8. The apparatus of statement 1 wherein the distinct electrode connected by AC field is located in the vicinity of the starting position for the macromolecule solution.

9. The apparatus of statement 1 wherein the distinct electrode connected by AC field is non-planar.

10. The apparatus of statement 8 wherein the distinct electrode is a nanopipette, preferably with attached conductive material, preferably in the form of a metalized nanopipette, more preferably wherein the metal is gold.

Statement 11. A method of concentration of macromolecules in a solution using the apparatus of statement 1.

12. The method of statement 10 wherein the concentration is caused by the DC field, preferably by dielectrophoresis.

13. The method of statement 10 wherein the concentration of macromolecules is centred around the opening to the cavity.

14. The method of statement 10 wherein the macromolecules to be concentrated are polarizable, preferably DNA, RNA or proteins, preferably solvated in.

15. The method of statement 10 wherein the concentration of the macromolecules in solution is >attoMolar.

The invention claimed is:

1. Apparatus for concentration and detection of polarizable analyte molecules within a fluid medium, the apparatus comprising:
a structure defining a cavity having an inlet and an outlet, the inlet having a cross-sectional dimension of between 3 nm and 200 nm;
a reservoir for the fluid medium adjacent to, and in fluid communication with, the inlet of the cavity, said reservoir having a proximal region;
a controller adapted to supply a direct current (DC) voltage and further adapted to supply a time varying voltage;
at least two translocation electrodes electrically coupled to the controller to receive said DC voltage and positioned relative to the structure to generate a DC translocation electric field passing through the cavity;
at least two trapping electrodes electrically coupled to the controller to receive the time varying voltage, one of the at least two trapping electrodes being positioned in the reservoir upstream of the inlet of the cavity and located on a central longitudinal axis of the cavity that passes through the inlet and the outlet of the cavity, and another of the at least two trapping electrodes being provided as a continuous layer on the surface of the structure adjacent to and surrounding the inlet of the cavity, such that a spacing of the at least two trapping electrodes defines a depth of the reservoir.

2. The apparatus of claim 1 in which the cavity defined by the structure comprises a nanopore.

3. The apparatus of claim 1 in which the structure defining the cavity comprises a pipette.

4. The apparatus of claim 1 in which the another of the at least two trapping electrodes being provided as the continuous layer on the surface of the structure adjacent to and surrounding the inlet of the cavity extends over the surface of the structure.

5. The apparatus of claim 1 in which the structure defining the cavity comprises any of: a solid-state structure; a dielectric material structure; a biological structure; and a hybrid biological structure-polymer structure.

6. The apparatus of claim 1 in which the controller is configured to cease supplying the time varying voltage before beginning to supply the DC voltage.

7. The apparatus of claim 1 in which the controller is configured to supply the time varying voltage and the DC voltage simultaneously to retard translocation.

8. The apparatus of claim 1 in which the time varying voltage has a frequency of 100 kHz-2 MHz.

* * * * *